United States Patent [19]

Tsuruoka et al.

[11] Patent Number: 5,515,449
[45] Date of Patent: May 7, 1996

[54] ENDOSCOPE IMAGE PROCESSING APPARATUS

[75] Inventors: Takao Tsuruoka; Kazunari Nakamura, both of Hachioji, Japan

[73] Assignee: Olympus Optical Co., Ltd., Tokyo, Japan

[21] Appl. No.: 842,769

[22] Filed: Mar. 2, 1992

Related U.S. Application Data

[63] Continuation of Ser. No. 440,620, Nov. 22, 1989, abandoned.

[30] Foreign Application Priority Data

Mar. 23, 1989 [JP] Japan ............................ 1-71245
Oct. 26, 1989 [JP] Japan ............................ 1-279094

[51] Int. Cl.$^6$ ...................................... G06K 9/00
[52] U.S. Cl. ............................ 382/128; 382/133; 348/45
[58] Field of Search .................... 382/6, 1, 128, 382/133, 134; 358/98; 128/6; 364/413.13, 413.15, 413.22; 348/45

[56] References Cited

U.S. PATENT DOCUMENTS

| | | | |
|---|---|---|---|
| 4,807,033 | 2/1989 | Keesen et al. | 358/166 |
| 4,901,143 | 2/1990 | Uehara et al. | 358/98 |
| 4,914,512 | 4/1990 | Sekiguchi | 358/98 |
| 4,922,915 | 5/1990 | Arnold et al. | 382/6 |
| 4,934,339 | 6/1990 | Kato | 358/98 |
| 4,962,540 | 10/1990 | Tsujiuchi et al. | 382/17 |
| 5,078,150 | 1/1992 | Hara et al. | 358/98 |

FOREIGN PATENT DOCUMENTS 63-173182  7/1988  Japan.

*Primary Examiner*—Yon J. Couso
*Attorney, Agent, or Firm*—Armstrong, Westerman, Hattori, McLeland & Naughton

[57] ABSTRACT

The endoscope image processing apparatus includes a processing apparatus for image-processing as predetermined at least one image signal and a discriminating apparatus for discriminating regions ineffective to image-processing by the processing apparatus or to the result of the image-processing from other effective regions. The image processing apparatus further includes an outputting apparatus for outputting the results of processing images by the processing apparatus only on the effective regions discriminated by the discriminating apparatus and an image forming apparatus forming images based on the results of processing images by the processing apparatus only on the effective regions.

6 Claims, 24 Drawing Sheets

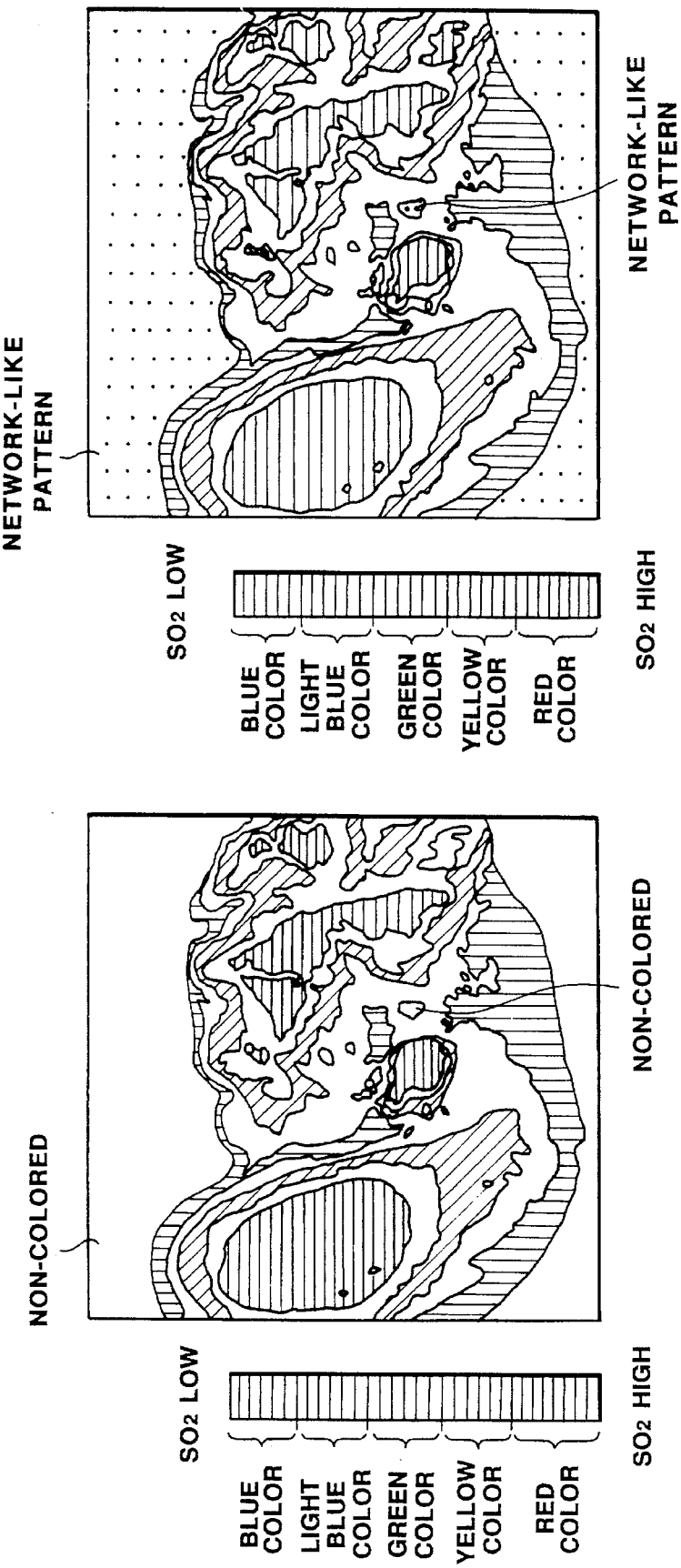

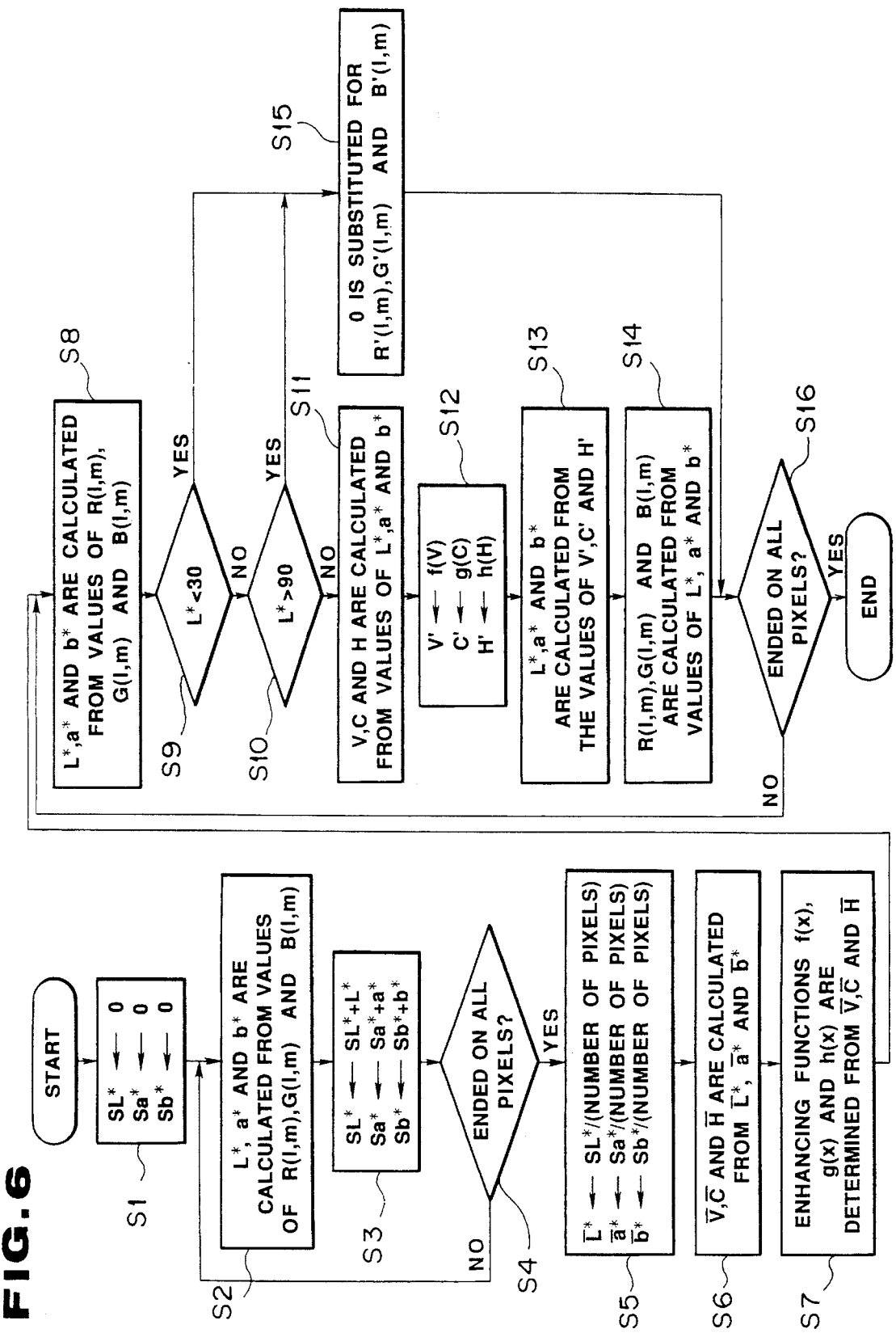

EDGES BY HALATION PARTS

EDGE BY LIVING BODY TISSUE

EDGES BY HALATION PARTS

EDGE BY LIVING BODY TISSUE

ENDOSCOPE IMAGE PROCESSING APPARATUS

This application is a continuation of application Ser. No. 440,620 filed Nov. 22, 1989, now abandoned.

BACKGROUND OF THE INVENTION

1. Field of the Invention

This invention relates to image processing apparatus for processing predetermined images and more particularly to an endoscope image processing apparatus for processing images obtained by an endoscope inserted into a body cavity to non-invasively diagnose affected parts.

2. Related Art Statement

Recently an endoscope, which can insert an elongate insertable part into a body cavity to observe organs within the body cavity or, as required, can make various therapeutic treatments using a treating instrument inserted through a treating instrument channel, has been extensively utilized.

Various electronic endoscopes have been suggested using an imaging means such as a solid state imaging device as a charge coupled device (CCD).

An example of a conventional endoscope apparatus is shown in FIG. 26. As shown in this drawing, a light emitted from a lamp 31 is time-serially separated into the respective wavelength regions of R (red), G (green) and B (blue) by a rotary filter 33 having filters 33R, 33G and 33B transmitting the light of the respective wavelength regions of red (R), green (G) and blue (B) and rotated by a motor 33 and is emitted into an endoscope light guide 23 at the entrance end. This frame sequential illuminating light is led to the endoscope tip part by the above mentioned light guide 23, is emitted from this tip part and is radiated onto an object to be imaged. The returning light from the object by this illuminating light is made to form an image on a CCD 41 provided in the endoscope tip part 9 by an image forming optical system 22. An image signal from this CCD 41 is amplified to be on a voltage level in a predetermined range by an amplifier 42. The output of this amplifier 42 has γ corrected by a γ-correcting circuit 43, is then converted into a digital signal by an A/D converter 44 and is stored in respective memories 46R, 46G and 46B through a switching switch 45. The image signals stored the respective memories are read out by the timing of television signals and are converted into analog signals respectively by D/A converters 47R, 47G and 47B. These analog image signals together with a synchronizing signal SYNC from a synchronizing signal generating circuit 52 are transmitted to RGB signal output ends 49R, 49G and 49B. The thus obtained RGB signals are displayed on a monitor to make an endoscope observation. The above mentioned synchronizing signal is output from a synchronizing signal output end 49S and is input together with the RGB signals into the monitor.

Recently, various image processes are made for such an endoscope apparatus. As examples of such an image process, there a) a coloration enhancing process whereby three RGB signals are converted to be in uniform color spaces of the brightness, chroma and hue and are processed to be enhanced as is shown in the publication of Japanese Patent Application Laid Open No. 173182/1988 and b) an operating process whereby a part of three RGB signals is changed to be in an infrared region and the oxygen saturated degree in the living body tissue is determined by an operation between pixels as is mentioned in U.S. Pat. No. 4,878,113.

However, in the conventional image process, the entire picture is uniformly processed. That is, regions which are not in proper exposure ranges such as a halation part and shadow part and even a region in which no effective precision is obtained due to the capacity and unit drop of the operating process means in the operating process are displayed as processed. Therefore, the region which is reliable in the processed image and the the region which is not reliable are difficult to discriminate from each other and have caused misconception.

OBJECT AND SUMMARY OF THE INVENTION

An object of the present invention is to provide an endoscope image processing apparatus whereby a region which does not meet a required precision can be distinguished. Misconception can therefore be prevented and information having high reliability can be obtained.

The endoscope image processing apparatus of the present invention comprises a processing device for image-processing as predetermined at least one image signal, a discriminating device for discriminating regions ineffective to image-processing by the above mentioned processing device or to the result of the image-processing from other effective regions, an outputting device for outputting the result of the image-processing by the processing device only on the effective regions discriminated by the above mentioned discriminating device and an image forming device for forming an image based on the result of the image-processing by the processing device only on the effective regions.

The other features and advantages of the present invention will become apparent with, the following explanation.

BRIEF DESCRIPTION OF THE DRAWINGS

FIGS. 1 to 4 relate to the first embodiment of the present invention.

FIG. 1 is a block diagram showing the formation of an image processing part.

FIG. 2 is an explanatory view showing an entire endoscope apparatus.

FIG. 3 is a block diagram showing the formation of an endoscope apparatus.

FIGS. 4(a)–4(d) are explanatory views for explaining an image process by this embodiment.

FIGS. 5 to 7 relate to the second embodiment of the present invention.

FIG. 5 is a block diagram showing the formation of an endoscope apparatus.

FIG. 6 is a flow chart showing a coloration enhancing process.

FIGS. 8 to 10 are flow charts showing hemoglobin amount calculating processes.

FIG. 11 is an explanatory view showing an output image by this embodiment.

FIGS. 12 and 13 relate to the fourth embodiment of the present invention.

FIG. 12 is a block diagram showing the formation of an image processing part.

FIG. 16 is a block diagram showing the formation of an endoscope apparatus.

FIG. 17 is a block diagram showing the formation of a color lag detecting circuit.

FIG. 18 is a waveform diagram showing the operation of a color lag detecting circuit.

FIG. 19 is a block diagram showing the formation of an endoscope apparatus.

FIG. 20 is a characteristic diagram showing input and output characteristics of an LUT circuit.

FIG. 22 is a block diagram showing the formation of an endoscope apparatus.

FIG. 23 is a characteristic diagram showing the transmitting characteristics of the respective filters of a rotary filter.

DETAILED DESCRIPTION OF THE PREFERRED EMBODIMENTS

In FIGS. 1 to 4 show the first embodiment of the present invention.

Figure 2:
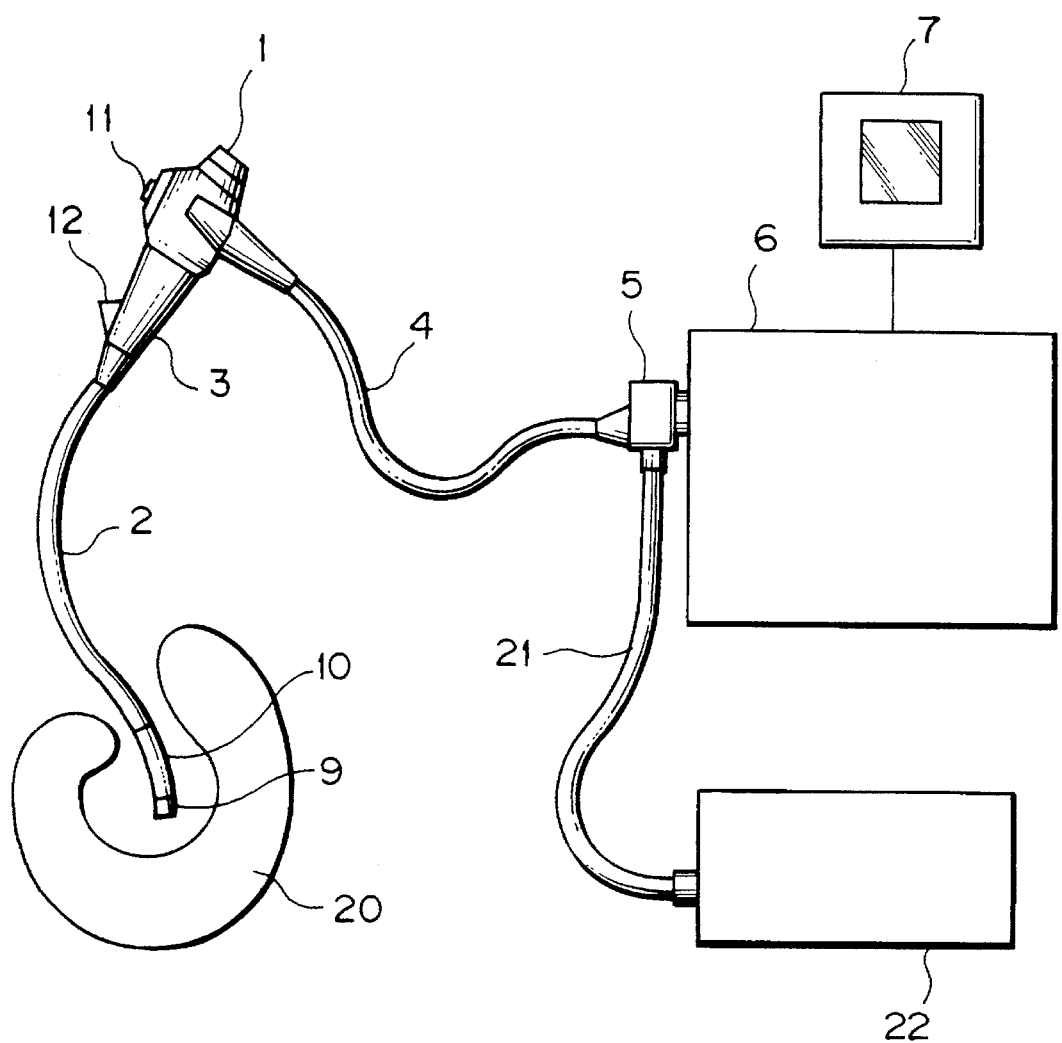

As shown in FIG. 2, an electronic endoscope 1 is provided with an elongate and, for example, flexible insertable part 2 to be inserted into a living body 20, a thick operating part 3 connected to this insertable part 2 at the rear end, a flexible universal cord 4 extended sidewise from the rear end part of the above mentioned operating part and a connector 5 at the tip of this universal cord 4. The above mentioned electronic endoscope 1 is to be connected through the above mentioned connector 5 to an observing apparatus 6 having a light source apparatus and signal processing circuit built-in. To the above mentioned observing apparatus 6 are to be connected an observing monitor 7 and various signal processing apparatuses (not illustrated). Also, to the above mentioned connector 5 is connected a suction tube 21 which is to be connected to a sucker or aspirator 22.

On the tip side of the above mentioned insertable part 2, a rigid tip part 9 and a curvable part 10 adjacent to this tip part 9 and curvable on the rear side are sequentially provided. The above mentioned operating part 3 is provided with a curving operation knob 11 by rotation of which the above mentioned curvable part 10 can be curved vertically and horizontally. An inserting port 12 communicates with a treating instrument channel provided within the above mentioned insertable part. Also, within the above mentioned insertable part 2, there is provided a suction channel which is to be connected to the above mentioned suction tube 21.

Figure 3:
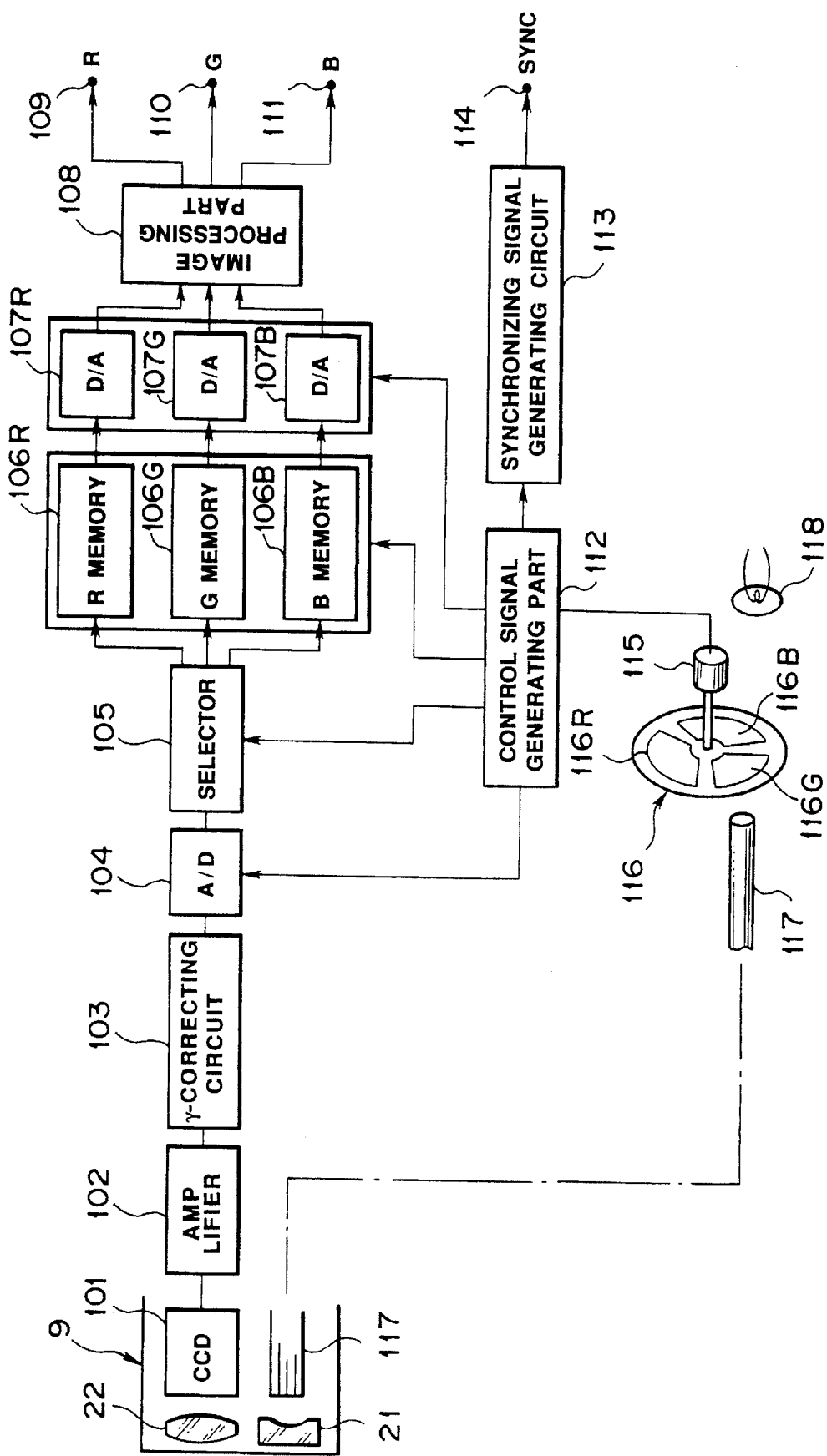

As shown in FIG. 3, a light distributing lens and an image forming optical system 22 are arranged in the above mentioned tip part 9. A light guide 117, made of a fiber bundle, is provided on the rear end side. The light guide 117 is inserted through the above mentioned insertable part 2, operating part 3 and universal cord 4 and is connected to the above mentioned connector 5 which is to be connected to the above mentioned observing apparatus 6 so that the illuminating light emitted from the light source apparatus within the observing apparatus 6 may enter the above mentioned light guide 117 at the entrance end. This light source apparatus is provided with a lamp 118 and a rotary filter 116 arranged in the illuminating light path and rotated by a motor 115. In this embodiment, the above mentioned lamp 118 is to emit ultraviolet to infrared rays. Filters 116R, 116G and 116B transmitting light of respective wavelength regions different from one another, are arranged in the peripheral direction in the above mentioned rotary filter 116. In this embodiment, the filter 116R transmits a red color light near 650 nm, the filter 116G transmits a green color light near 580 nm and the filter 116B transmits an infrared light near 800 nm. The light emitted from the above mentioned lamp 118 is time-serially separated by the above mentioned rotary filter 116 into the respective wavelength regions and enters the above mentioned light guide 117 at the entrance end. This illuminating light is led to the tip part 9 by the above mentioned light guide 117, is emitted from the tip surface and is radiated to the object through the light distributing lens 21.

A solid state imaging device as, for example, a CCD 101 is arranged in the image forming position of the above mentioned image forming optical system 22 so that the object image illuminated by the above mentioned frame sequential illuminating light may be formed by the above mentioned image forming optical system 22 and may be converted to an electric signal by the above mentioned CCD 101. The image signal from this CCD 101 is input into an amplifier 102 so as to be amplified into an electric signal in a predetermined range (for example, of 0 to 1 volt). The output electric signal of this amplifier 102 has γ corrected by a γ-correcting circuit 103, is then converted to a digital signal by an A/D converter 104 and is input into a selector 105 having one input and three outputs. The time-serially transmitted RGB signals are separated by this selector 105 into respective R, G and B color signals which are stored in respective memories 106R, 106G and 106B corresponding to R, G and B. The image signals read out of the respective memories are converted into anolog signals respectively by D/A converters 107R, 107G and 107B and are output from respective R, G and B signal output ends 109, 110 and 111 through an image processing part 108. Together with the above mentioned R, G and B signals, a synchronizing signal SYNC from a synchronizing signal generating circuit 113 is output from a synchronizing signal output end 114. The above mentioned R, G and B signal and synchronizing signal are input into the monitor 7 and various image processing apparatuses.

A control signal generating part 112 controlling the destination of the image signal and the transfer timing at the time of transferring the image signal is provided and delivers control signals to the above mentioned A/D converter 104, selector 105, respective R,G and B memories 106R, 106G and 106B, D/A converters 107R, 107G and 107B, synchronizing signal generating circuit 113 and motor 115.

The formation of the above mentioned image processing part 108 shall be explained in the following with reference to FIG. 1.

In this image processing part 108, the RGB signals output respectively from the above mentioned D/A converters 107R, 107G and 107B are passed respectively through inverted γ-correcting circuits 201R, 201G and 201B and are then input into respective level adjusting circuits 202R, 202G and 202B and a level adjusting control signal generating circuit 203. The control signal from the above mentioned level adjusting control signal generating circuit 203 is input to the above mentioned respective level adjusting circuits 202R, 202G and 202B. The outputs from the above mentioned level adjusting circuits 202R, 202G and 202B are input respectively into logarithmic amplifiers 204R, 204G and 204B. The signals from the logarithmic amplifiers 204R and 204G are input into a differential amplifier 205 and the signals from the logarithmic amplifiers 204G and 204B are input into a differential amplifier 26. The outputs of the above mentioned respective differential amplifiers 205 and 206 are input into a divider 207 whose output is input into a selector 208 at one input end. The output from this selector 208 is passed through a γ-correcting circuit 209 and is then output as RGB signals.

An ineffective region detecting circuit 210 for detecting the overflow and underflow in each operating process is provided and is connected to the logarithmic amplifiers 204R, 204G and 204B, differential amplifiers 205 and 206 and divider 207. The output of the above mentioned ineffective region detecting circuit is input into an abnormal part data ROM 211 in which predetermined abnormal part data are to be stored. The output of this abnormal part data ROM 211 is input into the above mentioned selector 208 at the other input end. The above mentioned selector 208 is to have the input switched by the control signal from the above mentioned ineffective region detecting circuit 210. That is to say, in an ordinary case, a signal from the divider 207 will be detected. In case a signal showing that an ineffective region is detected is output from the ineffective region detecting circuit 210, a signal from the abnormal part data ROM 211 will be selected.

The operation of this embodiment shall be explained in the following with reference to FIG. 4.

An ultraviolet to infrared light emitted from the lamp 118 enters the rotary filter 116 rotated by the motor 115. As described above, this rotary filter 116 has the filter 116R transmitting a red color light near 650 nm, filter 116G transmitting a green color light near 580 nm and filter 116B transmitting an infrared light near 800 nm. Therefore, the light from the above mentioned lamp 118 is time-serially separated into light of wavelengths corresponding to the above mentioned respective filters 116R, 116G and 116B which are input into a body cavity through the light guide 117 and are radiated as illuminating light into a body cavity through the light distributing lens 21. The object image by the respective illuminating light is formed on the CCD 101 by the image forming optical system 22 and is converted into an electric signal. The output signal of this CCD 101 is amplified by the amplifier 102 and is converted by the γ correcting circuit 103 to be of a predetermined γ characteristic. The output of this γ-correcting circuit 103 is converted into a digital signal by the A/D converter 104, is time-serially separated into respective wavelengths through the selector 105 and is stored as images in the memories 106R, 106G and 106B. The video signals read out of these memories 106R, 106G and 106B are synchronized, are converted into analogue video signals by the D/A converters 107R, 107G and 107B and are input into the image processing part 108.

The image processing part 108 in this embodiment is to obtain an image showing a variation of the oxygen saturated degree (which shall be mentioned as $SO_2$ hereinafter) of hemoglobin.

It is already known that, with the variation of $SO_2$, the spectral characteristic of hemoglobin will vary, that is, the spectral characteristic (light absorbing degree) of blood will vary. This variation of the light absorbing degree of blood with the variation of $SO_2$ depends on the difference between the spectral characteristics of oxyhemoglobin and deoxyhemoglobin. That is to say, near 580 nm and near 800 nm, with the variation of $SO_2$, the light absorbing degree of blood will hardly vary but, near 650 nm, with the variation of $SO_2$, the light absorbing degree of blood will vary. Therefore, the variation Of $SO_2$ can be determined with the images by these three wavelength regions.

The video signals corresponding to the above mentioned three wavelength regions are input into the image processing part 108 to obtain the image thus showing the variation of $SO_2$. The respective input signals are input respectively into the inverse γ correcting circuits 201R, 201G and 201B and, as they have already had γ corrected in the above mentioned γ correcting circuit 103, these signals are inverse γ corrected. The outputs of these inverse γ correcting circuits 201R, 201G and 201B are input respectively into the level adjusting circuits 202R, 202G and 202B which are adjusted in the levels by a level adjusting control signal from the level adjusting control signal generating circuit 203 and the entire level adjustment is made by the three level adjusting circuits 202R, 202G and 202B. As the variation of the light absorbing degree of blood by the variation of $SO_2$ is a log axis, the outputs of the level adjusting circuits 202R, 202G and 202B are logarithmically converted by the logarithmic amplifiers 204R, 204G and 204B. The outputs of the two logarithmic amplifiers 204R and 204G among these three logarithmic amplifiers 204R, 204G and 204B are input into the differential amplifier 205 and the difference between the video signals corresponding to the two wavelengths (near 650 nm and near 580 nm) is obtained. In the same manner, the outputs of the two logarithmic amplifiers 204G and 204B are input into the differential amplifier 206 and the difference between the video signals corresponding to the two wavelengths (near 580 nm and near 800 nm) is obtained.

This means that the difference between the video signal, corresponding to the region in which the light absorbing degree of blood hardly varies with the variation of $SO_2$, and the video signal corresponding to the region in which the light absorbing degree of blood varies with the variation of $SO_2$ is determined. How much oxygen is dissolved in the object, that is, the oxygen saturated degree is determined from them. The outputs of the above mentioned two differential amplifiers 205 and 206 are input into the divider 207 and $SO_2$ is determined by a predetermined operation. The output signal of this divider has γ corrected again by the γ correcting circuit 209 through the selector 208 and is output as RGB signals. In this case, the RGB signals are identical and a black and white image is output.

In this embodiment, such abnormalities as the overflow and underflow in the respective operation processes of the logarithmic amplifiers 204R, 204G and 204B, differential amplifiers 205 and 206 and divider 207 are detected by the ineffective region detecting circuit 210. In the operation processes, for example, of the logarithmic amplifiers 204R, 204G and 204B, when the input signal is very low, the operation result will be of an abnormal value but, when it is very high, the possibility of being a halation will be so high as to be determined to be of an abnormal value. In the operation processes of the differential amplifiers 205 and 206, in case the output of the differential amplifier 205 is to be divided by the output of the differential amplifier 206 in the divider 207 in the later step, if the output value of the differential amplifier 206 is near 0, the operatable range of the divider 207 will be exceeded and therefore when the output value of the differential amplifier 206 is near to 0, the output value determined will be to be abnormal. In the operation process of the divider 207, in case the operation output is minute, the part will be of a color close to a gray color and the possibility of no presence of hemoglobin in that part will be so high that such a case will be determined to be abnormal. Thus, in each operation process, in case the predetermined signal level is exceeded, a signal will be output to the ineffective region detecting circuit 210 from the operation circuit. In case an abnormal operation is made in the operation process, a signal will be transmitted to the abnormals part data ROM 211 from this ineffective region detecting circuit 210 and a predetermined abnormal part signal will be output from this abnormal part data ROM 211. The selector 208 will select the signal from the divider 207 in the ordinary case but the signal from the abnormal part data ROM 211 in case the signal is output from the ineffective region detecting circuit 210 and will output the signal to the γ correcting circuit 209.

Figure 4B:
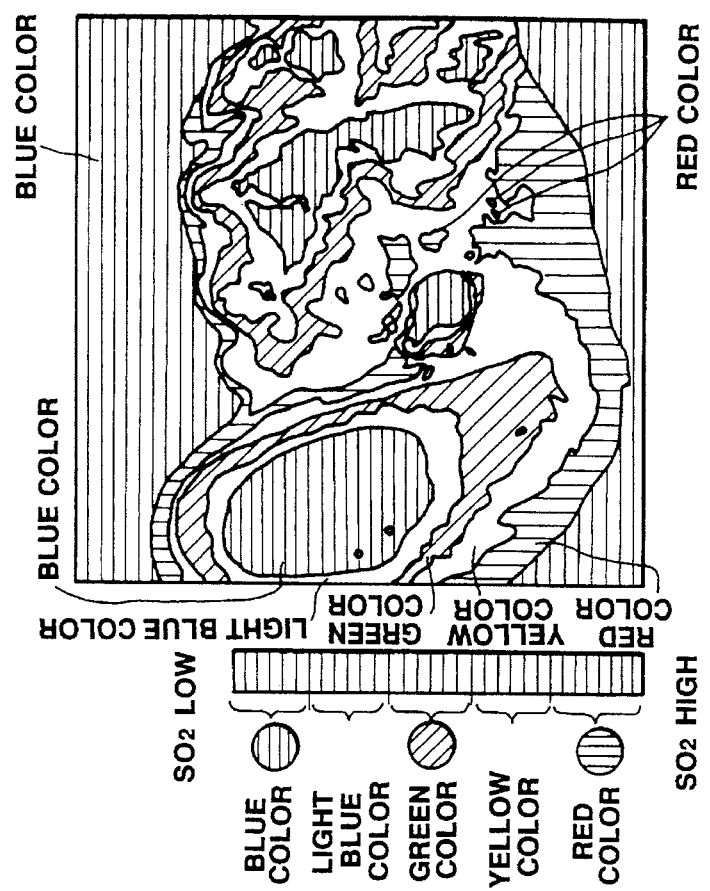
Figure 4A:
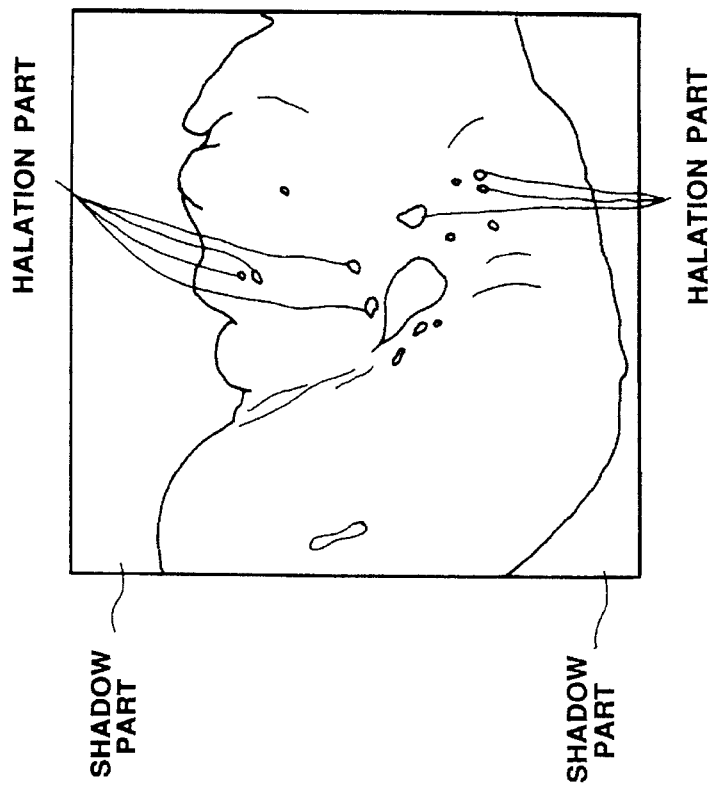

FIG. 4(a) shows an object image when the image is not processed in the image processing part 108. This image has very dark shadow parts and very bright halation parts. In these shadow parts and halation parts, even if the image is processed, no information having high reliability will be obtained.

FIG. 4(b) is of an image showing the variation of $SO_2$ as a result of processing the image even in such ineffective regions as the above mentioned shadow parts and halation parts the same as in the other regions as in the past. FIGS. 4(c) and (d) are of examples in which the image showing the variation of $SO_2$ as a result of processing the image outside the ineffective region, that is, in the effective region by the image processing part in this embodiment is formed and the ineffective region is displayed by another method than the normal displaying method.

The output image of the image processing part 108 shown in FIG. 3 is a black and white image but FIGS. 4(b) to (d) show images displayed by making the light and shade a pseudo-color. In fact, the variation of $SO_2$ is displayed, for example, in 32 colors varying steppedly but is simplified in these drawings to be shown in blue, light blue, green, yellow and red colors in the order mentioned from lower $SO_2$. These respective colors integrally represent such predetermined number of steps as are shown in FIG. 4(b). Also, in these drawings, only the blue, green and red color parts are hatched as shown in FIG. 4(b) but the other color parts are not hatched. However, as the colors vary in the arrangement shown in FIG. 4(b), the region between the two differently hatched regions will be of the color between the colors corresponding to the respective hatchings in the above mentioned arrangement.

In case even such ineffective regions as the shadow parts and halation parts are displayed by processing the image the same as in the other regions as shown in FIG. 4(b), for example, the shadow parts will be displayed in blue showing that $SO_2$ is low and the halation parts will be displayed in red showing that $SO_2$ is high and will cause misconception. $SO_2$ is low in the normal part of the tissue but is high on the periphery of an ulcer.

According to this embodiment, such ineffective regions as the above mentioned shadow parts and halation parts are displayed by a non-coloration as is shown in FIG. 4(c) or a network-like pattern as is shown in FIG. 4(d) based on the abnormal part signal stored in the abnormal part data ROM 211 so as to be able to be discriminated from the effective region and to be able to prevent the generation of misconception.

The displaying method is not limited to those shown in FIGS. 4(c) and (d). For example, in case the image showing the variation of $SO_2$ is displayed with a light and shade image without being made a pseudo-color, if the video signal is, for example, on the level of 0 to 255 (8 bits), the ordinary signal may be displayed by 50 to 255 and the ineffective region may be displayed by 0. Only the ineffective region may be periodically lighted and extinguished.

Thus, according to this embodiment, an ineffective region determined to be unreliable in the operation is detected and is displayed by any other method than the normal displaying method so that the generation of misconception may be prevented and a diagnosis information having high reliability may be provided. Also, as the part determined to be an ineffective region is not processed, the processing time can be reduced.

Figure 1:
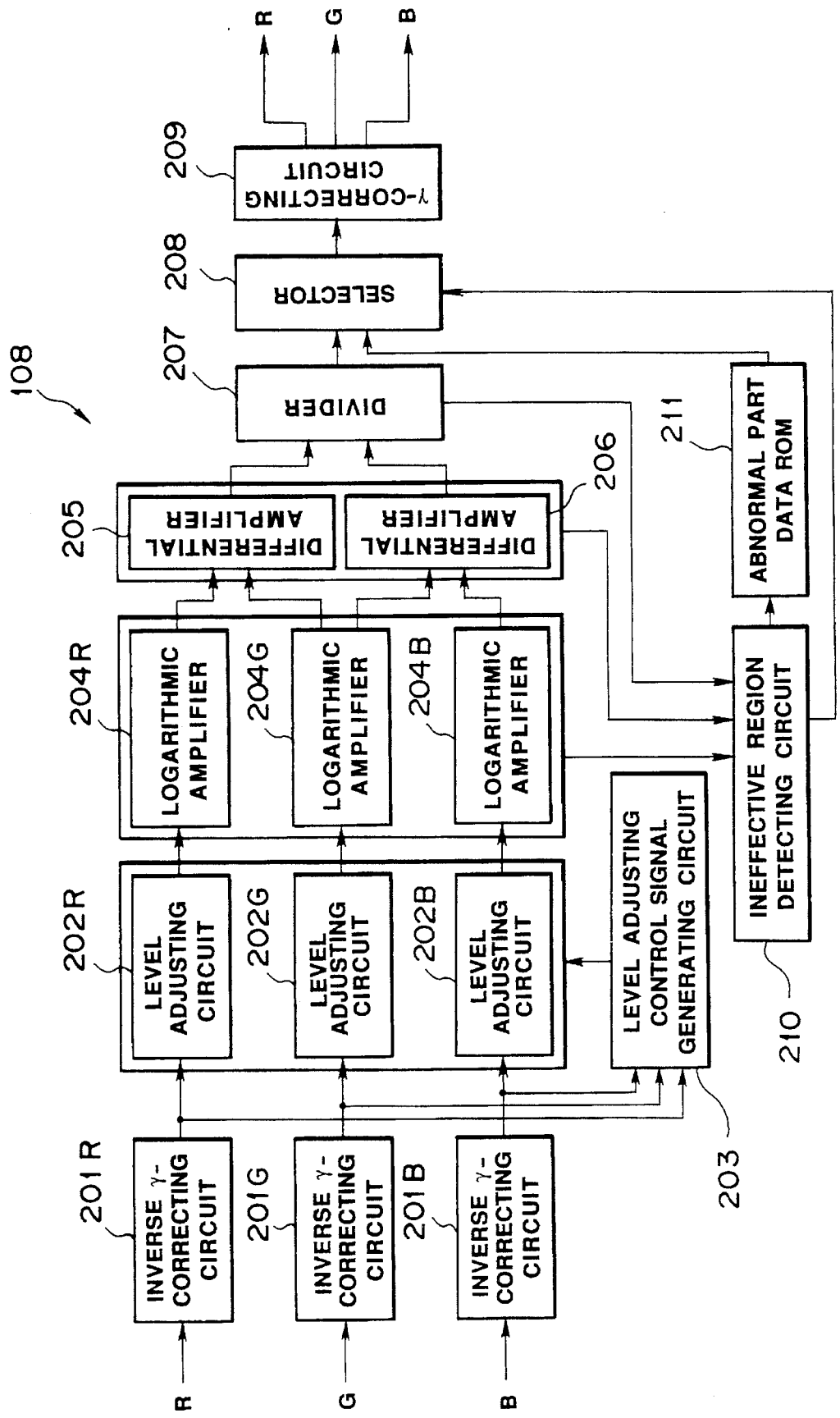

In the image processing part 108 shown in FIG. 1, the calculation is made with hardware but may be made with software by using an ordinary calculating machine.

Also, in this embodiment, three RGB signals are directly processed but may be initially recorded in a video tape or photodisc and then may be processed later.

This embodiment can be applied not only to RGB signals but also to a composite signal as of the NTSC standard.

Figure 5:
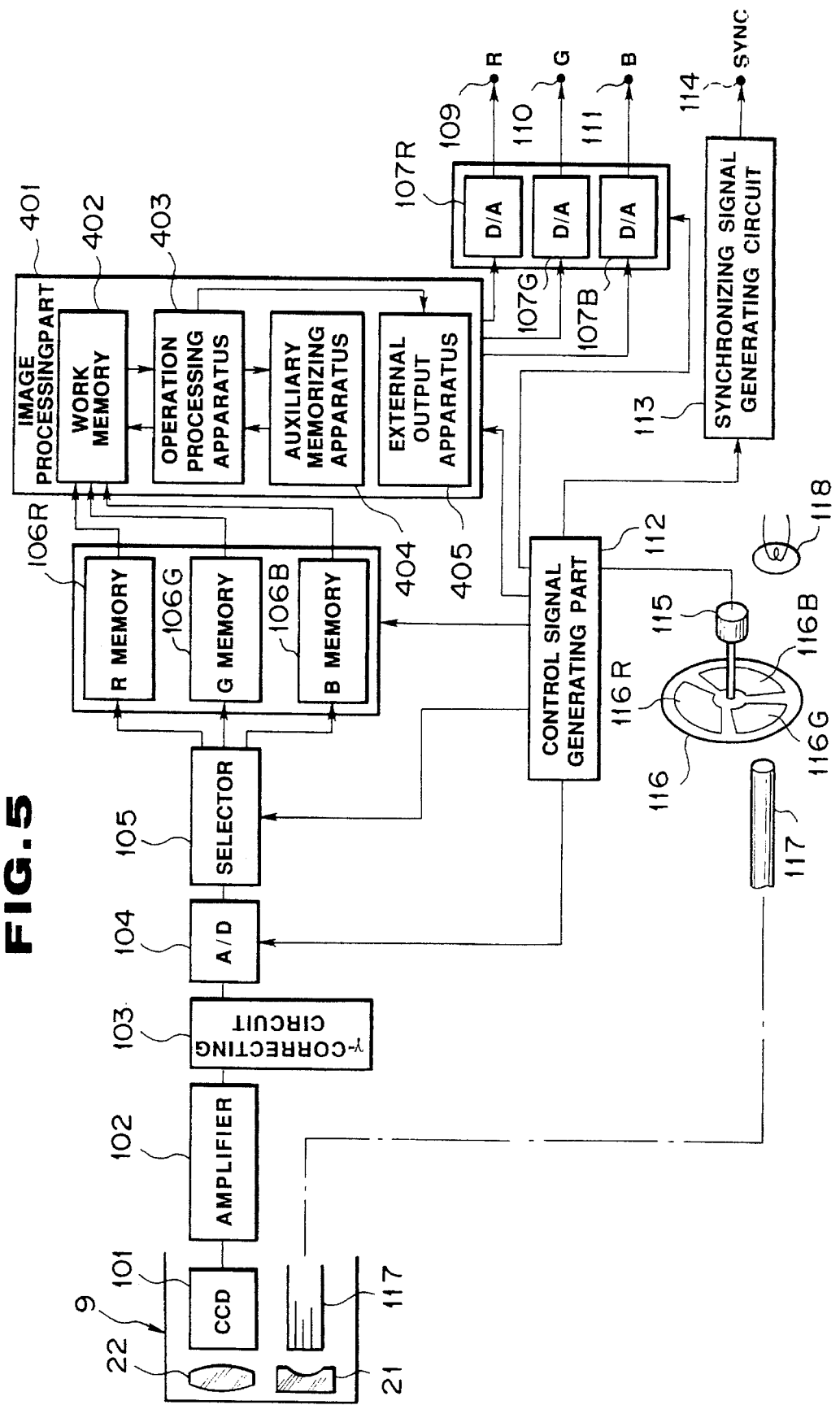

The second embodiment of the present invention is shown in FIGS. 5 to 7.

In this embodiment, as shown in FIG. 5, there is no image processing part 108 of the first embodiment but instead a new image processing part 401 is connected to the RGB memories 106R, 106G and 106B at the output thereof. The output signals of this image processing part 401 are converted to analogue signals by the D/A converters 107R, 107G and 107B and are output from the respective R, G and B signal output ends 109, 110 and 111.

The above mentioned image processing part 401 comprises a work memory 402, operation processing apparatus 403, auxiliary memorizing apparatus 404 and external output apparatus 405. The image data from the above mentioned RGB memories 106R, 106G and 106B are stored in the work memory 402 and the image data within this work memory 402 are processed by the operation processing apparatus 403 according to the program on the auxiliary memorizing apparatus 404. The image data from this image processing part 401 are output to the above mentioned D/A converters 107R, 107G and 107B.

The control signal from the control signal generating part 112 is input into the above mentioned image processing part 401.

In this embodiment, in the rotary filter 116, the filter 116R transmits a red color light, the filter 116G transmits a green color light and the filter 116B transmits a blue color light.

The other formations are the same as in the first embodiment.

The operation of this embodiment shall be explained in the following with reference to FIGS. 6 and 7.

The illuminating light separated time-serially into the light of the respective RGB wavelength regions by the rotary filter 116 is radiated to the object and, the same as in the first embodiment, the images corresponding to the respective wavelength regions are stored in the memories 106R, 106G and 106B. The respective images of the respective memories 106R, 106G and 106B are transmitted to the work memory 402 within the image processing part 401.

The operation processing apparatus 403 processes to enhance the coloration of the image within the above mentioned work memory 402 on a CIE L* a* b* uniform color space according to the procedure shown, for example, in FIG. 6. This coloration enhancing process shall be explained.

First of all, in Step S1, 0 is substituted in each of SL*, Sa* and Sb*.

Then, in Step S2, L*, a* and b* are calculated from the values of the respective RGB components R(l,m), G(l,m) and B(l,m) of the original image.

Then, in Step S3, SL*+L* is made SL*, Sa*+a* is made Sa* and Sb*+b* is made Sb*.

Then, in Step S4, it is determined whether the process has ended on all the pixels or not. In the case of NO, the process will return to the above mentioned Step S2 and, in the case of YES, the process will proceed to the next Step S5.

In these Steps S2 to S4, the total sum of SL*, Sa* and Sb* on all the pixels of L*, a* and b* are determined.

Then, in Step S5, the above mentioned SL*, Sa* and Sb* are divided respectively by the number of pixels to obtain average colors $\overline{L^*}$, $\overline{a^*}$ and $\overline{b^*}$.

Then, in Step S6, the average values $\overline{V}$, $\overline{C}$ and $\overline{H}$ of the brightness, colored degree and hue are calculated and determined from the above mentioned $\overline{L^*}$, $\overline{a^*}$ and $\overline{b^*}$.

Then, in Step S7, enhancing functions f(x), g(x) and h(x) are determined from the above mentioned average values $\overline{V}$, $\overline{C}$ and $\overline{H}$.

Then, in Step S8, L*, a* and b* are calculated from the values of the respective RGB components R(l,m), G(l,m) and B(l,m) of the original image.

Then, in Step S9, it is determined whether the brightness component L* is smaller than 30 or not. In the case of YES, the process will proceed to Step S15. In the case of NO, the process will proceed to Step S10. In the above mentioned Step S10, it is determined whether the brightness component L* is larger then 90 or not. In the case of YES, the process will proceed to Step S15. In the case of NO, the process will proceed to Step S11.

In Step S11, the brightness, coloration and hue V, C and H are determined by the calculation from the above mentioned L*, a* and b*.

Then, in Step S12, the above mentioned V, C and H are converted to V', C' and H' respectively by the enhancing functions f(x), g(x) and h(x).

Then, in Step S13, L*, a* and b* are calculated from the values of V', C' and H'.

Then, the respective RGB components R'(l,m), G'(l,m) and B'(l,m) after the process are determined by the calculation from the values of L*, a* and b*.

Then, in Step S16, it is determined whether the process has ended on all the pixels or not. In the case of NO, the process will return to the above mentioned Step S8. In the case of YES, the process will end.

On the other hand, in the case of YES in the above mentioned Steps S9 and S10, in Step S15, 0 will be substituted respectively in R'(l,m), G'(l,m) and B'(l,m) and the process will proceed to the above mentioned Step S16.

By the way, V=L*, H=tan$^{-1}$ (b*/a*) and C={(a*)$^2$+ (b*)$^2$}$^{1/2}$.

In the process shown in FIG. 6, the values of L*, a* and b* are calculated from the data of R, G and B of the original image, their average values are determined, the functiops for the enhancement are determined, the values of L*, a* and b* are again calculated from the data of R, G and B of the original image, V, C and H are determined, are enhanced and are converted to the data of R, G and B to make an image of the result of the process. The details of this process are shown in the publication of Japanese patent application laid open No. 173182/1988.

Figure 7A:
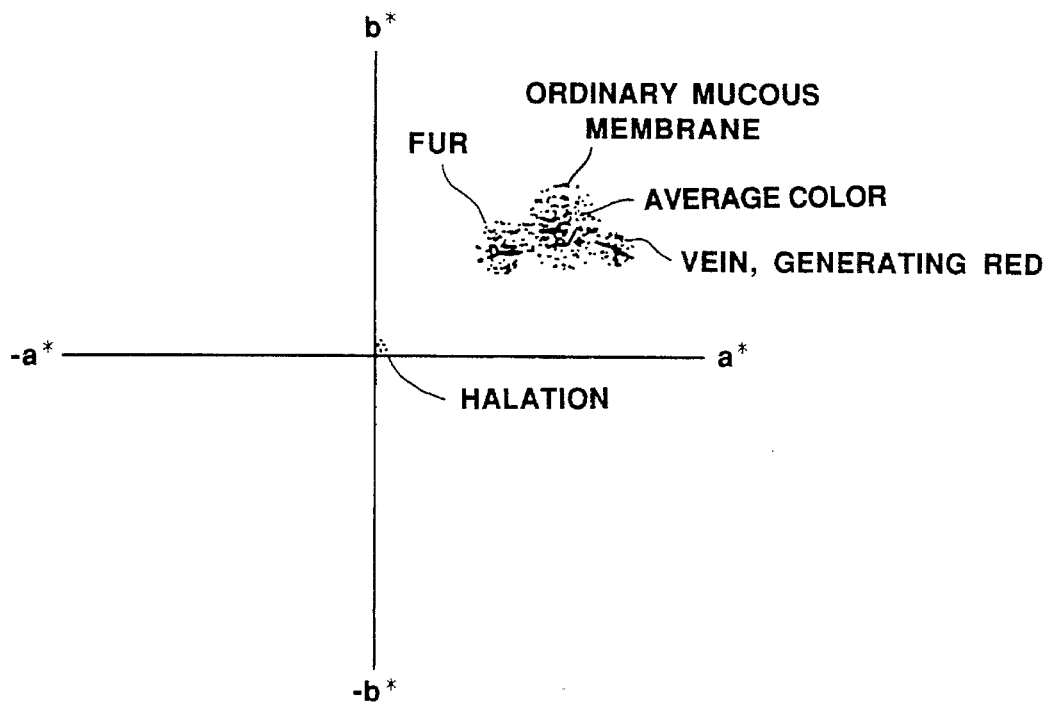
FIGS. 7(a) and 7(b) are explanatory views showing the results of the coloration enhancing process.
Figure 7B:
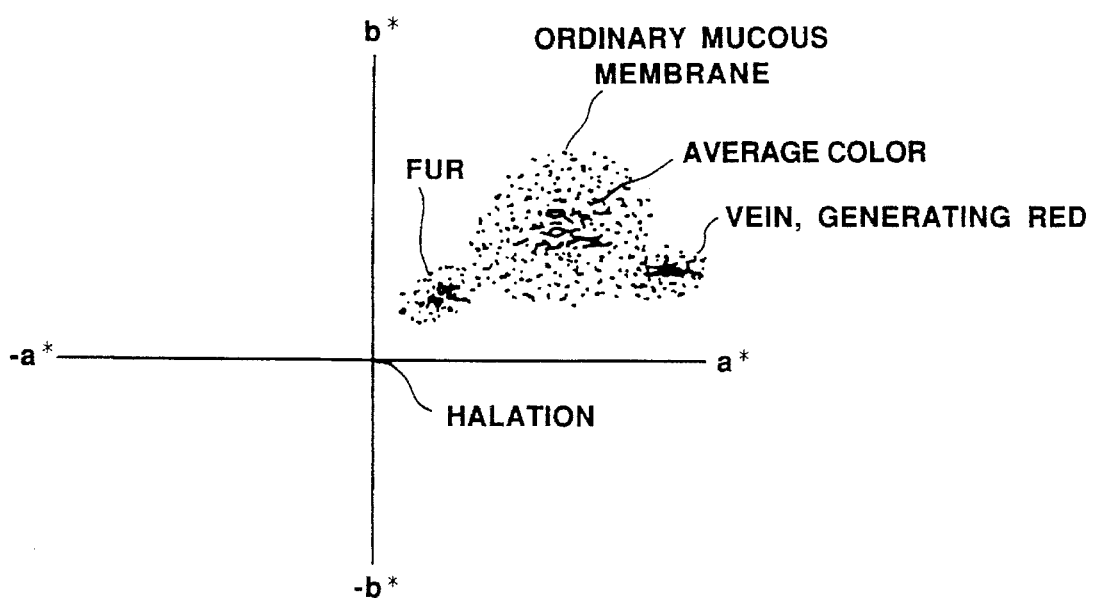

The variation of the coloration by this process is shown in FIG. 7. FIG. 7(a) shows the distribution of data in the L*a*b* coordinate system and FIG. 7(b) shows the distribution of data in the L*a*b* coordinate system after the process. As shown in these drawings, in the image as a result of the process, the color difference between the respective average values of the distribution of the data of an ordinary mucous membrane and the distribution of such data as of the vein, red generation and fur expands to be wider and to be easier to discriminate than in the original image.

In such a color tone enhancing process, in this embodiment, on the basis of L* representing the brightness component, the shadow part in which L* is below 30 and high light part in which it is above 90 are detected and are displayed other than the normal displaying method. For example, by making a black and white non-coloration, the region determined to be unreliable can be determined and misconception can be prevented.

Also, as the ineffective region part is not processed, the processing time can be reduced.

A process result can be stored, as required, in such an auxiliary memorizing apparatus 404 as a magnetic disc and can be output to such an external output apparatus 405 as a video printer.

The other operations and effects are the same as in the first embodiment.

In FIGS. 8 to 11 is shown the third embodiment of the present invention.

The formation of the endoscope apparatus of this embodiment is fundamentally the same as in the second embodiment shown in FIG. 5 but is different only in the transmitting characteristics of the respective filters of the rotary filter 116 and the algorithm of the process made in the image processing part 401.

The same as in the first embodiment, in the above mentioned rotary filter 116, the filter 116R transmits a red color light near 650 nm, the filter 116G transmits a green color light near 580 nm and the filter 116B transmits an infrared light near 800 nm. The light from the lamp 118 is time-serially separated into the light of the wavelengths corresponding to the above mentioned respective filters 116R, 116G and 116B and is radiated to an object to be imaged. The output signal of the CCD 101 imaging the object image is time-serially separated into three RGB signals corresponding to the above mentioned respective wavelengths and is stored in the memories 106R, 106G and 106B. The respective images in the respective memories 106R, 106G and 106B are transferred to a work memory 402 within the image processing part 401.

Figure 8:
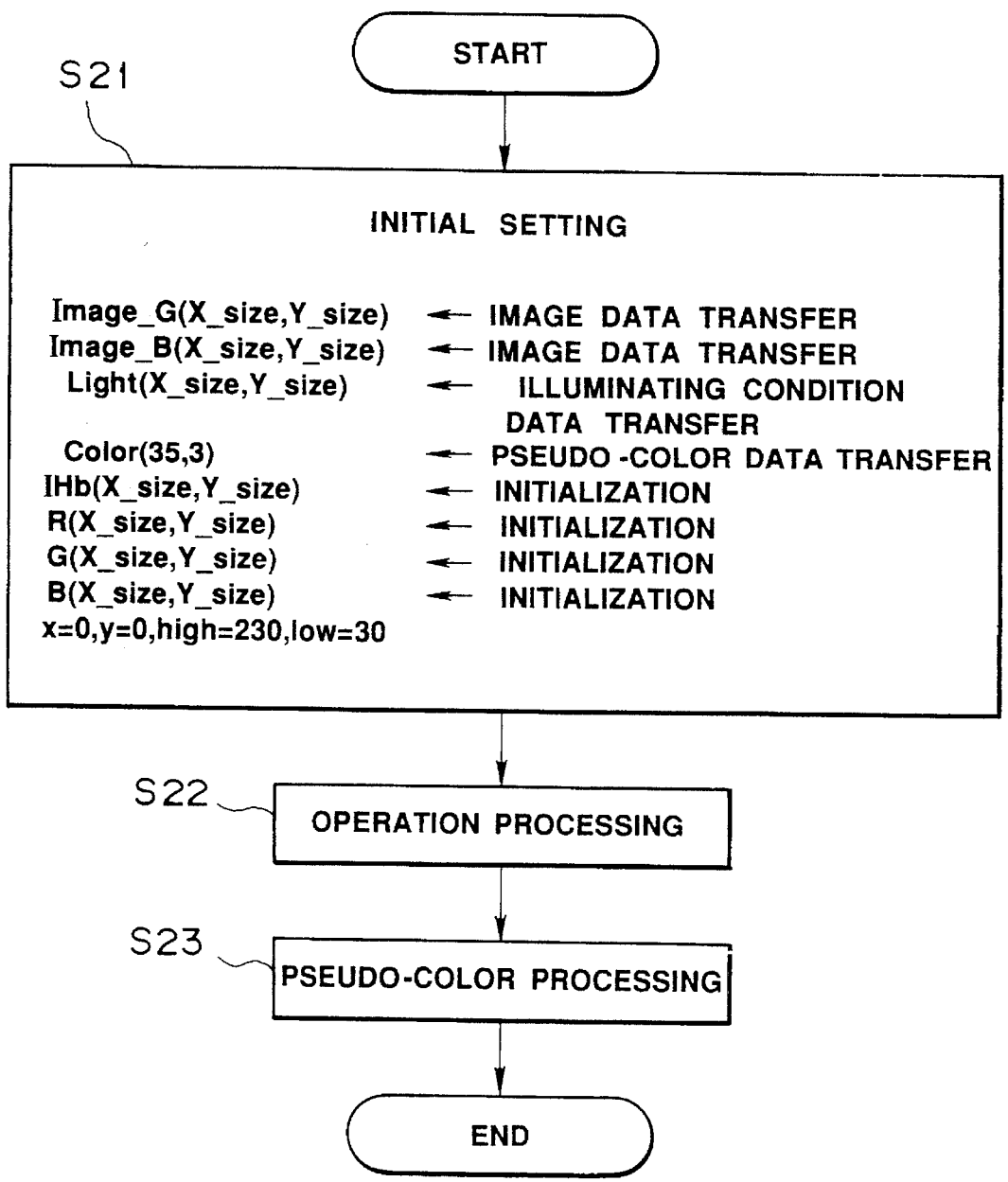
FIGS. 8 to 11 relate to the third embodiment of the present invention.
Figure 9:
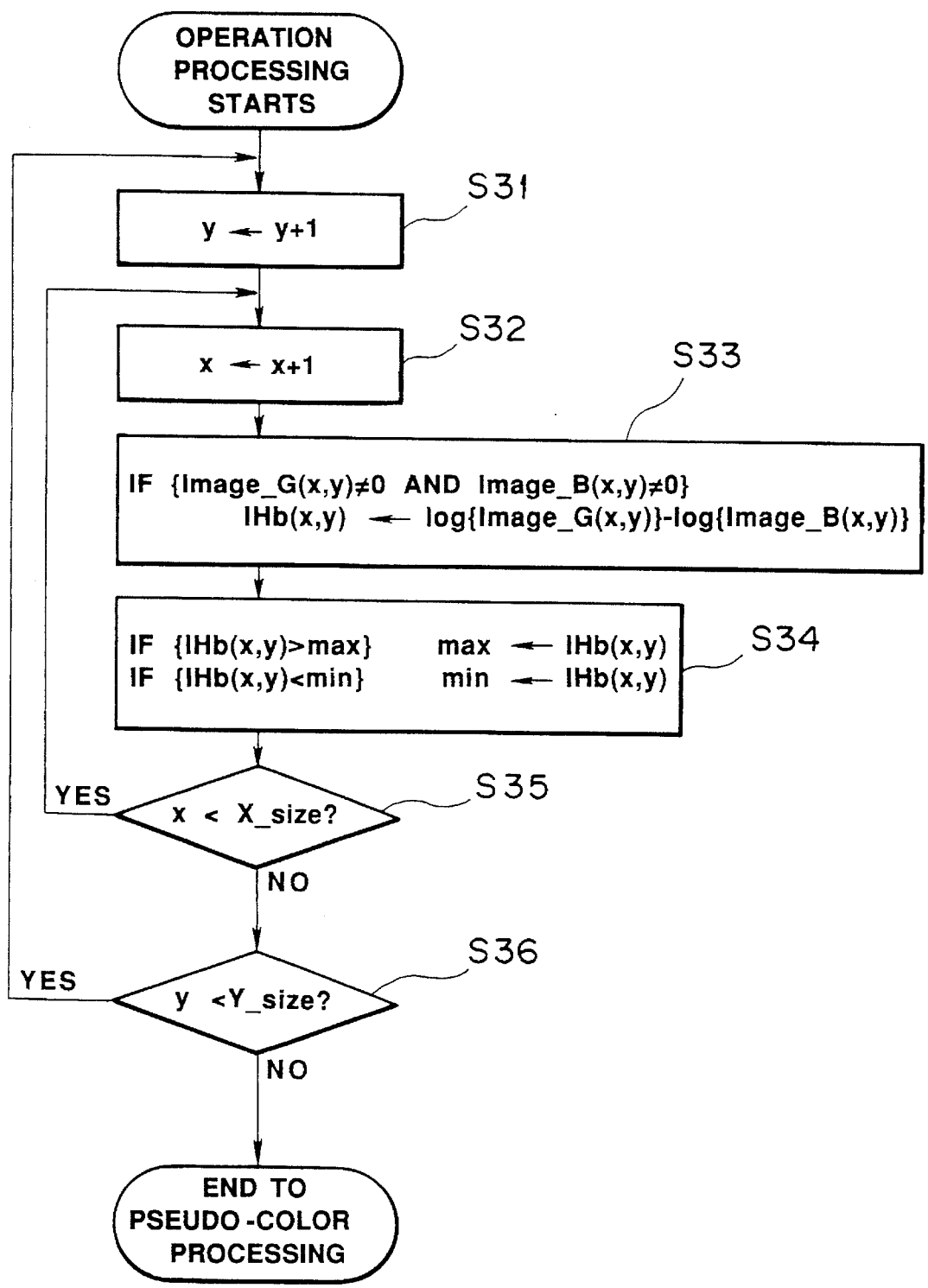
Figure 10:
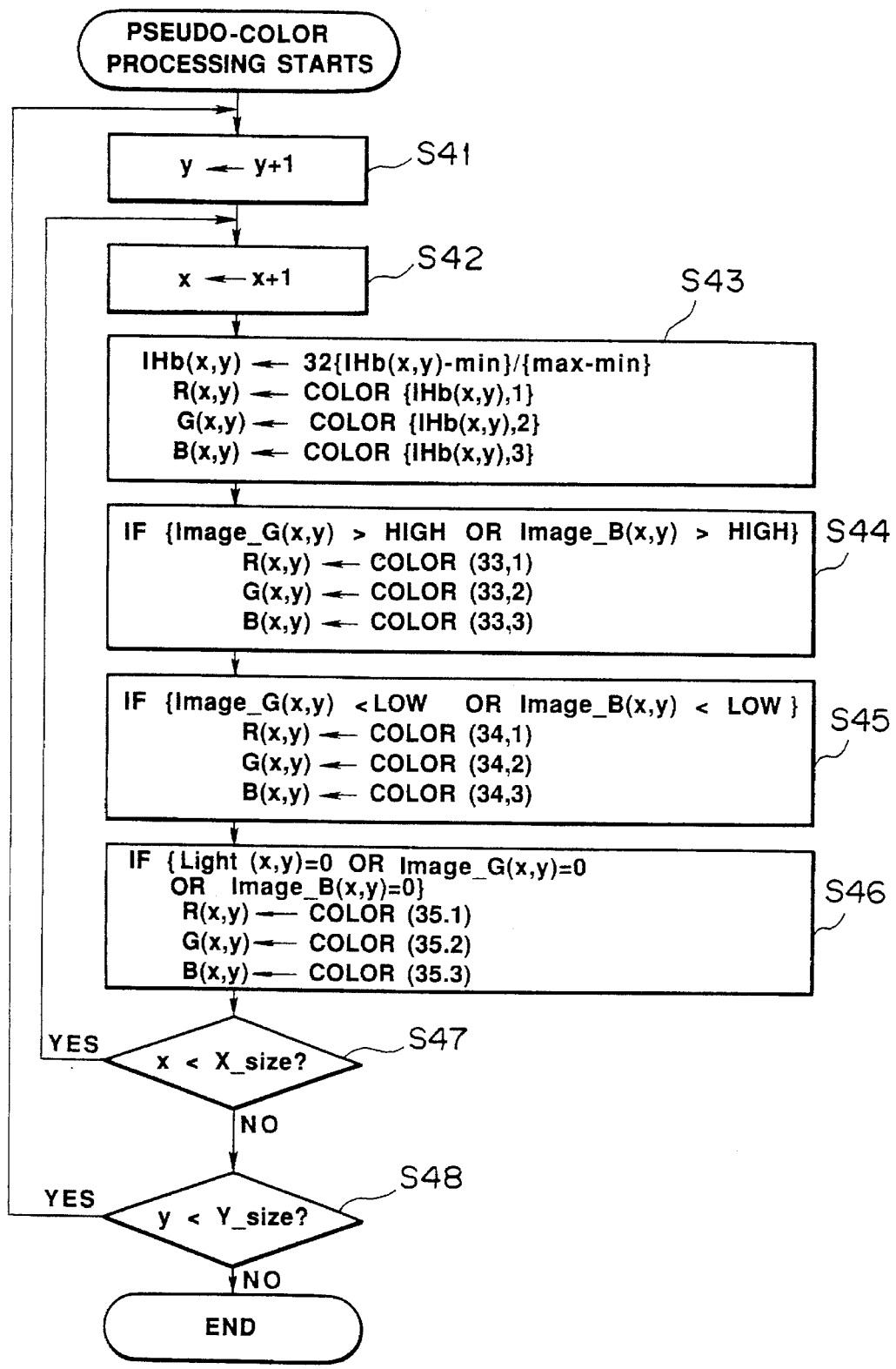
Figure 11:
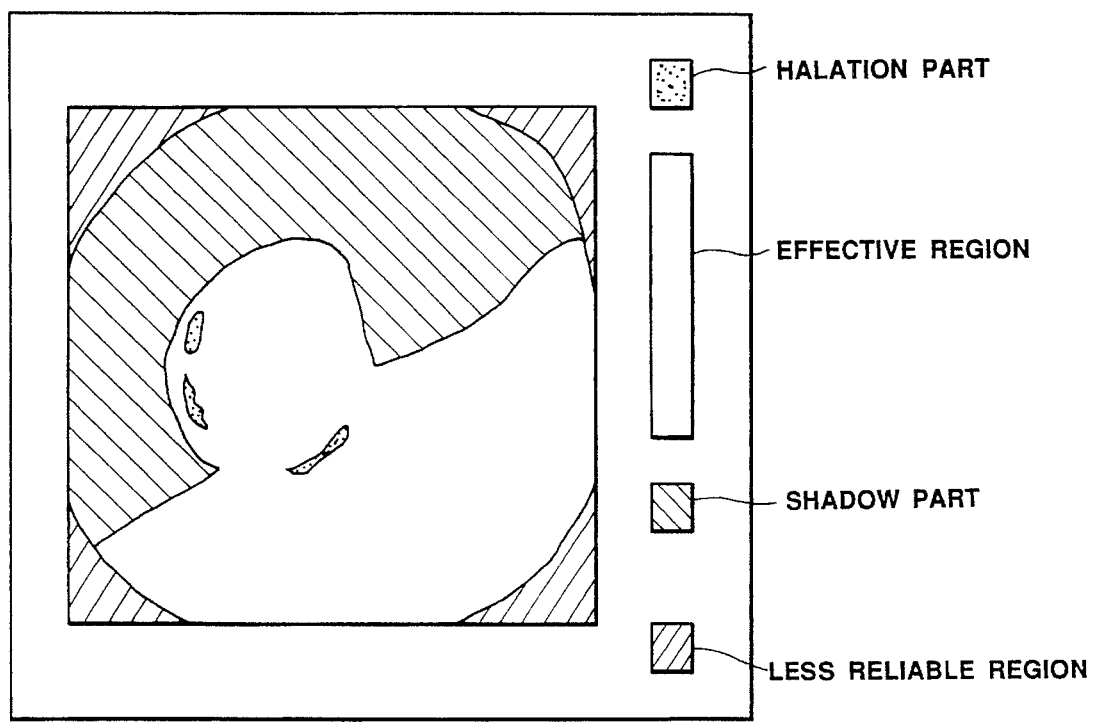

An operation processing apparatus 403 within the image processing part 401 calculates the hemoglobin amount according to the procedure shown in FIGS. 8 to 10 for the image within the work memory 402. This process shall be explained in the following.

As shown in FIG. 8, the hemoglobin amount calculating process is to first make an initial setting in Step S21, to then make an operation process in Step S22 and to lastly make a pseudo-color process in Step S23.

In the above mentioned initial setting, by transferring the image data, the G component Image _G (X _ size, Y _size) and B component Image _B(X _size, Y size) of the original image are set. Also, a hemoglobin amount housing array IHb (X _size, Y _size) and pseudo-color data housing arrays R (X _size, Y _size), G (X _size, Y _size) and B (X _size, Y _size) are prepared and are respectively initialized. Also, the illuminating condition data are transferred to an array Light (X _size, Y _size). This Light (X _size, Y size) has data in which a reference white color plate such as of magnesium oxide is photographed, a region in which the light amount is less than ½ the light amount in the center part is made 0 and the other region is made 1. Thirty-two kinds of quasi-color data and 3 kinds of ineffective region displaying data are stored respectively for RGB in an array Color (35, 3). For example, when 1 to 32 are made normal data and 33 to 35 are made ineffective region data, the data of the above mentioned Light X _size, Y_ size) and Color (35, 3) will be read out of an auxiliary memorizing apparatus 405. Also, work variables x, y, high and low are initialized to be respectively 0, 0, 230 and 30.

Then, in the operating process, as shown in FIG.9, first of all, in Step S31, y+1 is made y and then, in Step S32, x+1 is made x.

Then, in Step S33, if an Image _G and Image _B are not both 0, log (Image G (X,Y)}–log (Image _B (X,Y)} will be determined to be IHb (X,Y).

Then, in Step S34, if IHb (X,Y)>max, IHb (X,Y) will be made max and, if IHb (X,Y)<min, IHb (X,Y) will be made min.

Then, in Step S35, it is determined whether x<X _ size or not. In the case of YES, the process will return to Step S32 but, in the case of NO, the process will proceed to the next Step S36. In this Step S36, it is determined whether y<Y _size or not. In the case of YES, the process will return to Step S31 but, in the case of NO, the operation process will end and will proceed to a pseudo-color process.

Thus, in the operation process, the hemoglobin amount IHb is calculated on all the pixels in which the Image _G and Image _B are not both 0 and the maximum value and minimum value of IHb are determined respectively as max and min. The vicinity of 580 nm, to which the G image corresponds, is a wavelength region in which the light absorbing degree of blood (hemoglobin) is large and the vicinity of 800 nm to which the B image corresponds is a wavelength region in which the light absorbing degree of blood is small. Therefore, the hemoglobin amount is determined by the operation between these two images.

Then, in the pseudo-color process, as shown in FIG. 10, first of all, in. Step S41, y+1 is made y and then, in Step S42, x+1 is made x.

Then, in Step S43, when 32 (IHb (X,Y)–min }/{max–min } is made IHb (X,Y), IHb will be normalized to be 0 to 32. The pseudo-color data Color {IHb (X,Y), 1}, Color {IHb (X,Y), 2 } and Color {IHb (X,Y), 3} corresponding to this normalized IHb are read out of the color array and are substituted respectively into R (X,Y), G (X,Y) and B (X,Y).

Then, in Step S44, in case at least one of the Image _G and Image _B is higher than the prescribed value (for example, 230 if 8-bit data), it will be determined to be a halation part and ineffective region displaying data, that is, in this case, the 33rd data Color (33, 3), Color (33, 2) and Color (33, 3) are substituted respectively into R (X,Y), G (X,Y) and B (X,Y).

Then, in Step S45, in case at least one of the Image _G and Image _B is lower than the prescribed value (for example, 30 if 8-bit data), it will be determined to be a shadow part and ineffective region displaying data, that is, in this case, the 34th data Color (34, 1), Color (34, 2) and Color (34, 3) are substituted respectively into R (X,Y), G (X,Y) and B (X,Y).

Then, in Step S46, the part in which Light (X,Y) is 0, that is, the part in which the illuminating condition is deteriorated and the part in which at least one of the Image _G and Image _B is 0, that is, the part in which the operation process is impossible are considered to be parts in which the precision can not be guaranteed and ineffective region displaying data, that is, in this case, 35th data Color (35, 1), Color (35, 2) and Color (35, 3) are substituted respectively into R (X,Y), G (X,Y) and B (X,Y).

Then, in Step S47, it is determined whether x<X _ size or not. In the case of YES, the process will return to S42 but, in the case of NO, the process will proceed to the next Step S48. In this Step S48, it is determined whether y<Y _size or not. In the case of YES, the process will return to Step S41 but, in the case of NO, the hemoglobin amount calculating process will end.

Thus, according to this embodiment, the ineffective region which is not determined to be reliable in the operation is detected and is displayed by the other method than the normal displaying method so that misconception may be prevented from being generated. Also, as the ineffective region is shown by a plurality of displaying methods in response to the ineffective reason, by what reason the region is determined to be ineffective can be easily recognized. As a displaying method, as shown, for example, in FIG. 11, the three ineffective regions of the halation part, shadow part and low reliability part are represented by three kinds of non-coloration and the reliable effective regions are represented by 32 kinds of coloration.

The number of displayed colors of the ineffective regions and effective regions are not limited to the above mentioned examples but may be altered freely as required. Also, not only the color display but also the black and white display will do. In this case, it is considered to display the ineffective regions with a plurality of network-like patterns.

The other formations, operations and effects are the same as in the first or second embodiment.

Figure 12:
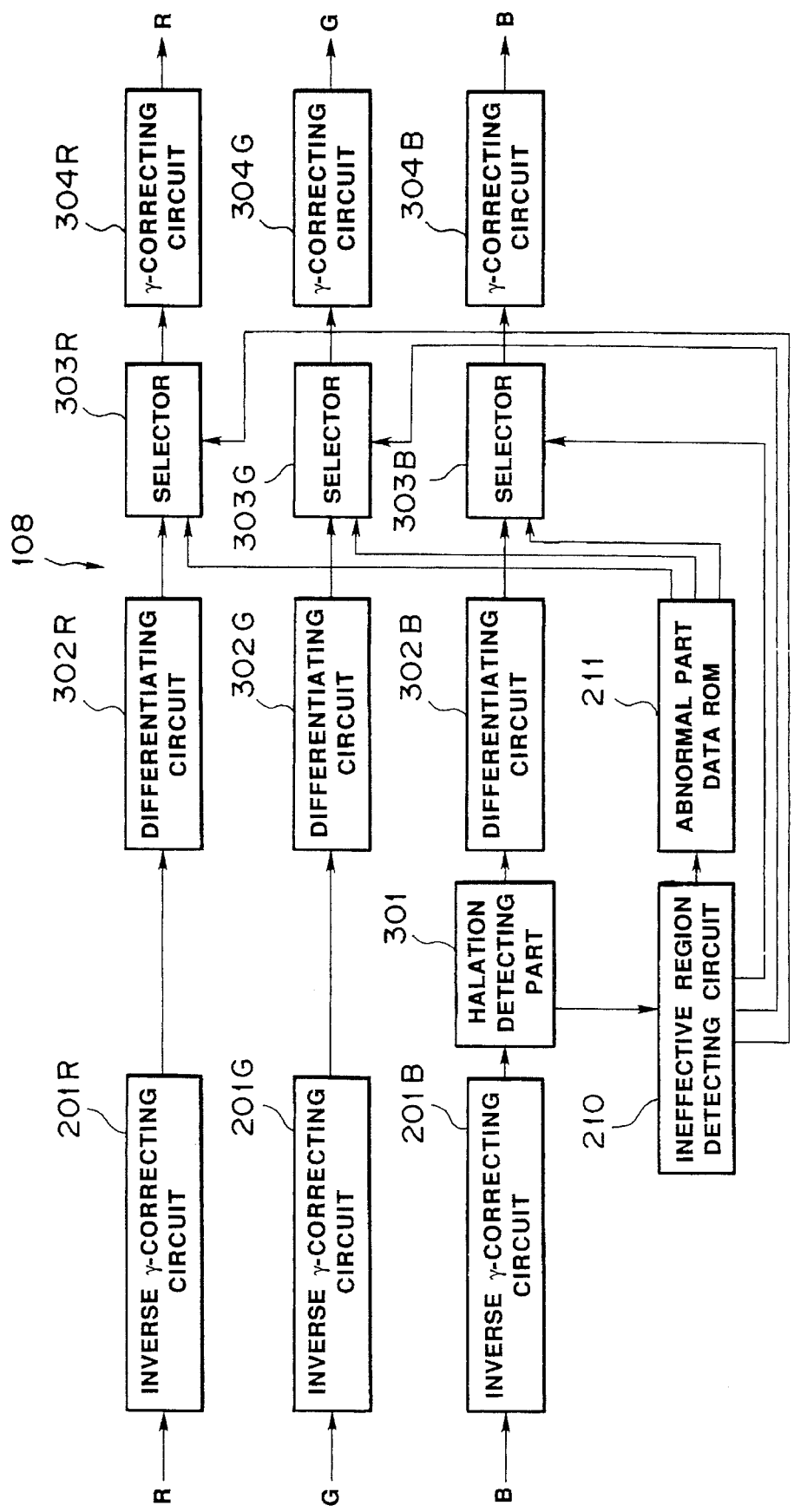

In FIGS. 12 and 13 is shown the fourth embodiment of the present invention.

The formation of this embodiment is fundamentally the same as of the first embodiment but is different only in the transmitting characteristics of the respective filters of the rotary filter 116 and the formation of the image processing part 108.

In the above mentioned rotary filter 116, the same as in the second embodiment, the filter 116R is to transmit a red color light, the filter 116G is to transmit a green color light and the filter 116B is to transmit a blue color light.

The image processing part 108 is of a formation as is shown in FIG. 12.

The RGB signals output from the D/A converters 107R, 107G and 107B in FIG. 3 are input respectively into inverse γ-correcting circuits 201R, 201G and 201B. The outputs of the inverse γ-correcting circuits 201R and 201G are input respectively into differentiating circuits 302R and 302G. The output of the inverse γ-correcting circuit 201B is input into a halation detecting part 301. The output of this halation detecting part 301 is input into a differentiating circuit 302B and ineffective region detecting circuit 210. The respective outputs of the above mentioned differentiating circuits 302R, 302G and 302G are output as RGB signals respectively through selectors 303R, 303G and 303B and γ-correcting circuits 304R, 304G and 304B. Also, the output of the above mentioned ineffective region detecting circuit 210 is output to an abnormal part data ROM 211 and selectors 303R, 303G and 303B. The above mentioned abnormal part data ROM 211 outputs abnormal part signals to the selectors 303R, 303G and 303B. The above mentioned selectors 303R, 303G and 303B select and output one of the outputs of the differentiating circuits 302R, 302G and 302B and output of the abnormal part data ROM 211 in response to the signal from the ineffective region detecting circuit 210.

The operation of this embodiment shall be explained in the following.

An edge extracting method is already known as one of endoscope image processes. This is to make a primary differentiation or secondary differentiation to extract only an edge component in an image and investigate the relationship between the structure of a living body tissue and an affected part. The image processing part 108 in this embodiment is to make the above mentioned edge extracting process.

As shown in FIG. 3, the video signals corresponding to the three RGB wavelength regions are input into the image processing part 108. As the respective input signals are input respectively into the inverse γ-correcting circuits 201R, 201G and 201B and have had γ already corrected by the γ-correcting circuit 103, an inverse γ-correction is made to uncorrect the image. The output of the inverse γ-correcting circuit 201B is input into a halation detecting part 301 and the halation part is detected from the level of the B signal. In an ordinary endoscope image, the B signal exists only in the low level region. In case the B signal is in the high level region, it will be able to be determined to be of a halation. That is to say, in the halation detecting part 301, the level of the B signal is monitored so that, in case it is in the high level region, a signal will be transmitted to the ineffective region detecting circuit 210.

The outputs from the inverse γ-correcting circuits 201R and 201G and halation detecting part 301 are processed to be differentiated respectively in the differentiating circuits 302R, 302G and 302B and only the edge part is extracted. The outputs of these differentiating circuits 302R, 302G and 302B have γ corrected again respectively by the γ-correcting circuits 304R, 304G and 304B through the selectors 303G, 303G and 303B and are output as RGB signals.

Figure 13A:
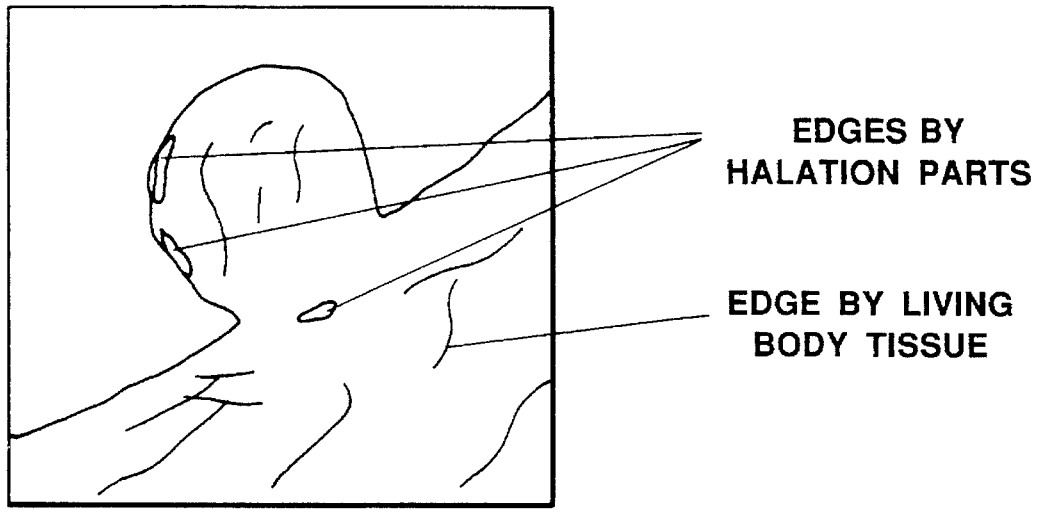
FIGS. 13(a) and 13(b) are explanatory views showing an image by a conventional edge extracting process and an output image by this embodiment.
Figure 13B:
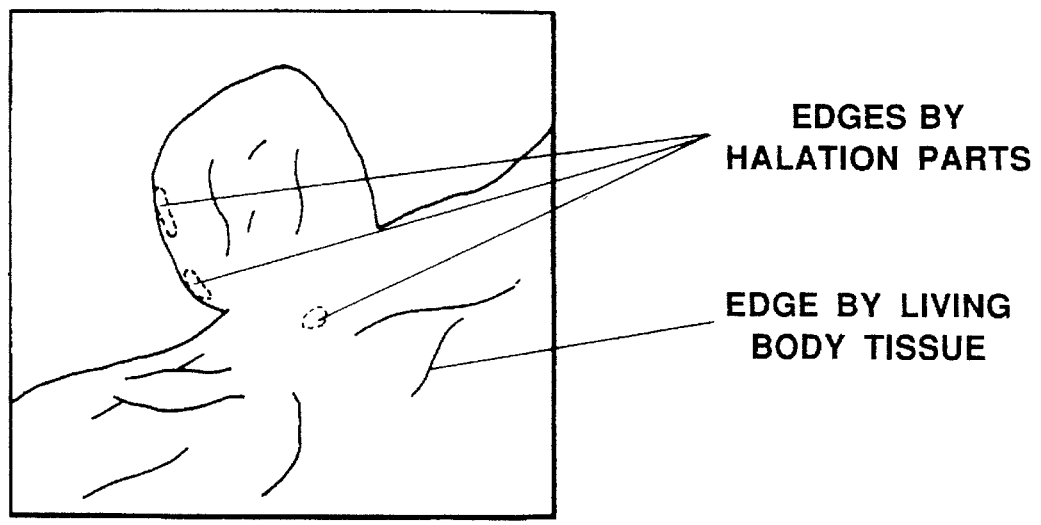

In case a halation is detected in the halation detecting part 301, a signal will be transmitted from the above mentioned ineffective region detecting circuit 210 to the abnormal part data ROM 211 from which predetermined part signals will be output to the selectors 303R, 303G and 303B. In these selectors 303R, 303G and 303B, in an ordinary case, signals from the differentiating circuits 302R, 302G and 302B will be selected but, in case a signal showing that a halation is detected is output from the ineffective region detecting circuit 210, a signal from the abnormal part data ROM 211 will be selected and will be output to the γ-correcting circuits 304R, 304G and 304B. An example of the output image by this embodiment is shown in FIG. 13(b) and, for the sake of comparison, an image by the conventional edge extracting process is shown in FIG. 13(a).

Thus, in this embodiment, the ineffective region of a halation part determined to be unreliable in the operation is detected and is displayed by the other method than the normal displaying method so that the edge component by a living body tissue and the edge component by a halation may be distinguished from each other and may be prevented from being misconceived. As a displaying method, the halation part may be considered to be represented by broken lines as shown, for example, in FIG. 13(b).

In this embodiment, as the halation is detected based on the level of the B signal, in case a dyeing or the like is made, the detecting precision will likely be reduced. In such a case, a luminance signal Y may be determined by the following formula from the three RGB signals and the halation may be detected from the level of this luminance signal Y:

$$Y = 0.31R + 0.59G + 0.11B.$$

The other formations, operations and effects are the same as in the first embodiment.

Figure 14:
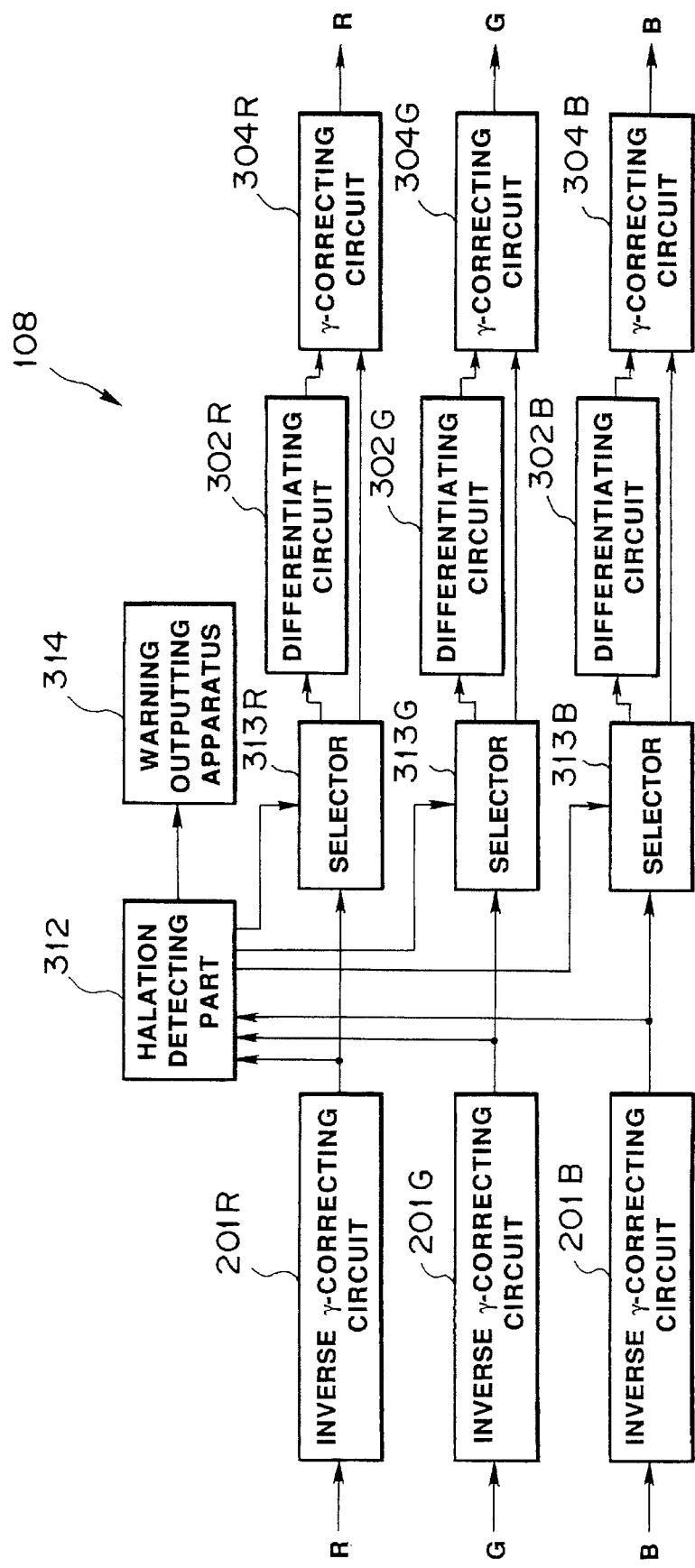
FIG. 14 is a block diagram showing the formation of an image processing part in the fifth embodiment of the present invention.

In FIG. 14 is shown the fifth embodiment of the present invention.

The formation of this embodiment is fundamentally the same as the first embodiment but is different only in the transmitting characteristics of the respective filters of the rotary filter 116 and the formation of the image processing part 108.

In the above mentioned rotary filter 116, the same as in the second embodiment, the filter 116R transmits a red color light, the filter 116G transmits a green color light and the filter 116B transmits a blue color light.

The image processing part 108 is formed as shown in FIG. 14.

The RGB signals output from the D/A converters 107R, 107G and 107B in FIG. 3 are input respectively into the inverse γ-correcting circuits 201R, 201G and 201B whose outputs are input into a halation detecting part 312 and selectors 313R, 313G and 313B. The outputs of the above mentioned halation detecting part 312 are input into a warning outputting apparatus 314 and the above mentioned selectors 313R, 313G and 313B. The above mentioned selectors 313R, 313G and 313B output the outputs of the inverse γ-correcting circuits 201R, 201G and 201B in response to the signals from the halation detecting part 312 selectively to the differentiating circuits 302R, 302G and 302B or γ-correcting circuits 304R, 304G and 304B. The outputs of the above mentioned differentiating circuits 302R, 302G and 302B are input into the above mentioned γ-correcting circuits 304R, 304G and 304B whose outputs are output as RGB signals.

The operation of this embodiment shall be explained in the following.

The image processing part 108 in this embodiment makes the same edge extracting process as in the fourth embodiment.

As shown in FIG. 3, video signals corresponding to the three RGB wavelength regions are input into the image processing part 108. The respective input signals are input respectively into the inverse γ-correcting circuits 201R, 201G and 201B, have had γ already corrected by the γ-correcting circuit 103 and therefore have inverse γ corrected to uncorrect it to the original state. The outputs of the inverse γ correcting circuits 201R, 201G and 201B are input into the halation detecting part 312 wherein a luminance signal Y is determined by the following formula from the three RGB signals and the halation is detected from the level of this luminance signal Y:

$$Y=0.31R+0.59G+0.11B.$$

That is to say, in the halation detecting part 312, the level of the luminance signal Y is monitored and the rate of the halation parts existing in one picture is determined so that, in case the rate becomes above a predetermined value (for example, 40%), a signal may be transmitted to the warning outputting apparatus 314 which is, for example, a warning lamp or warning buzzer. Thus, the user is warned that the input image has so many ineffective regions by halations as to be inproper to be processed. In case the rate of halation parts becomes above a predetermined value, the halation detecting part 312 will output control signals to the selectors 313R, 313G and 313B which will thereby transmit the outputs of the inverse γ-correcting circuits 201R, 201G and 201B as they are to the γ-correcting circuits 304R, 304G and 304B. That is to say, the input signals will not be processed at all and will be output as they are.

On the other hand, in case the rate of halation parts is below the predetermined value, the halation detecting part 312 will output control signals to the selectors 313R, 313G and 313B which will thereby transmit the outputs of the inverse γ-correcting circuits 201R, 201G and 201B to the differentiating circuits 302R, 302G and 302B. In this case, the RGB input signals will be processed to be differentiated respectively by the differentiating circuits 302R, 302G and 302B and only the edge part will be extracted. The outputs of these differentiating circuits 302R, 302G and 302B will have γ corrected again respectively by the γ-correcting circuits 304R, 304G and 304B and will be output as RGB signals.

Thus, in this embodiment, the ineffective regions of halation parts determined to be unreliable in the operation are detected. In case these ineffective regions are determined to be contained above a predetermined rate, a warning will be issued to stop the subsequent process so that the misconception may be prevented from being generated by processing an image improper to be processed.

In this embodiment, in case the rate of ineffective regions such as halation parts is above a predetermined value, a warning will be issued and the subsequent process will be automatically stopped but, after the warning is issued, whether the image is to be processed or not may be manually selected as by a switch.

The other formations, operations and effects are the same as in the first or fourth embodiment.

In the following sixth to ninth embodiments, the ineffective region and effective region are distinguished from each other before the image is processed.

Figure 15:
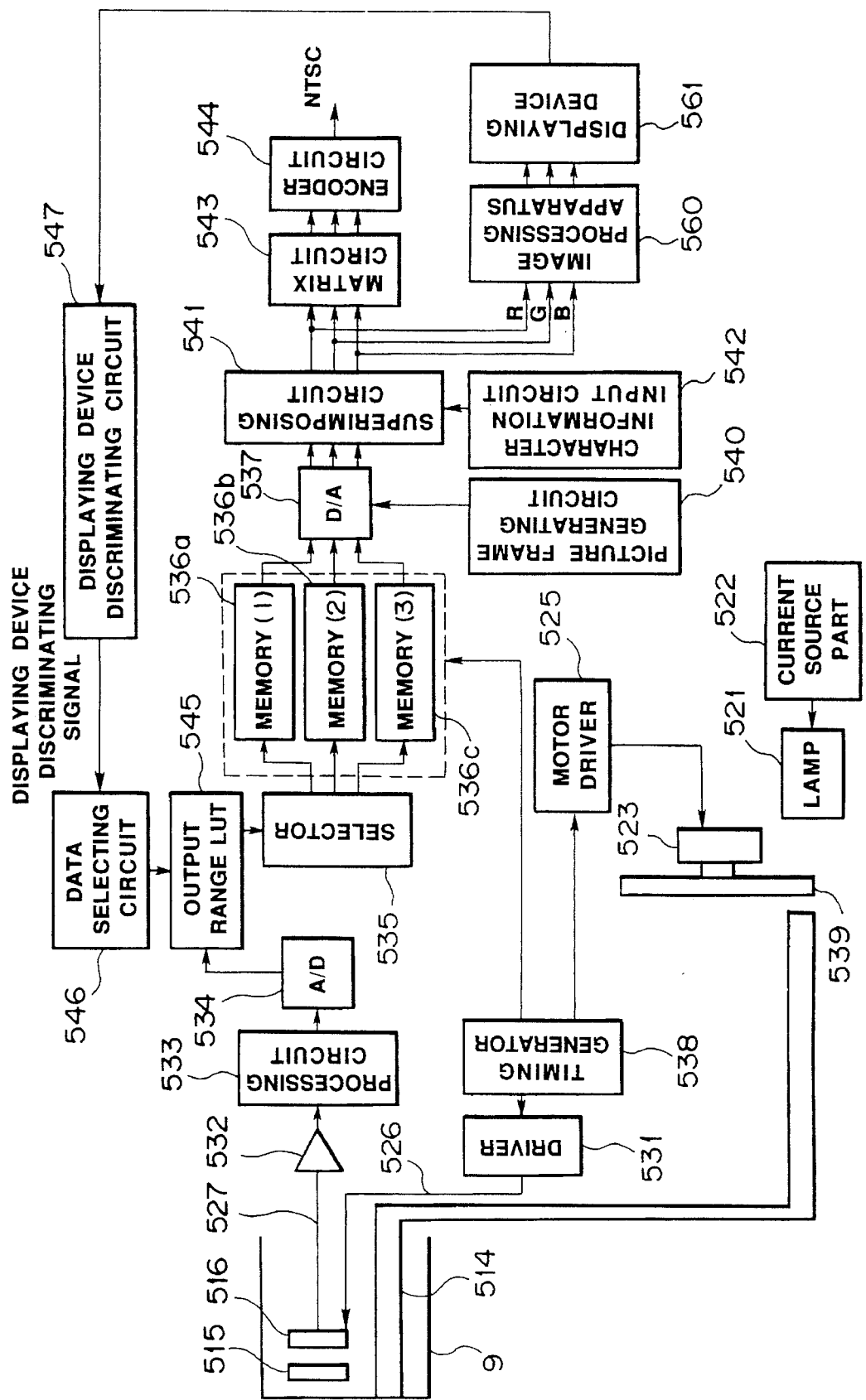
FIG. 15 is a block diagram showing the formation of an endoscope apparatus in the sixth embodiment of the present invention.

FIG. 15 shows the sixth embodiment of the present invention.

The general formation of an endoscope apparatus in this embodiment is the same as in FIG. 2.

As shown in FIG. 15, a light guide 514 transmitting an illuminating light is inserted through an insertable part 2 of an electronic endoscope 1. The tip surface of this light guide 514 is arranged in the tip part 9 of the insertable part 2 so that the illuminating light may be emitted from this tip part 9. Also, the above mentioned light guide 514 is inserted on the entrance end side through a universal cord 4 and is connected to a connector. An objective lens system 515 is provided in the above mentioned tip part 9. A solid state imaging device 516 is arranged in the image forming position of this objective lens system 516 and has a sensitivity in a wide wavelength range from an ultraviolet region including a visible region to an infrared region. The above mentioned solid state imaging device 516 is connected with signal lines 526 and 527 which are inserted through the above mentioned insertable part 2 and universal cord 4 and are connected to the above mentioned connector.

A lamp 521 generating light in a wide band from ultraviolet rays to infrared rays is provided within an observing apparatus (which shall be mentioned as a video processor hereinafter). For this lamp 521 can be used .a general xenon lamp or strobe lamp which generates a large amount of not only a visible light but also an ultraviolet light and infrared light. This lamp 521 is fed with an electric power by a current source part 522.

A rotary filter 539 rotated and driven by a motor 523 is arranged in front of the above mentioned lamp 523 and is provided as arranged in the peripheral direction with filters transmitting light of respective wavelength regions of red (R), green (G) and blue (B). The above mentioned motor 523 is driven as controlled in rotation by a motor driver 525.

The light transmitted through the above mentioned rotary filter 539 and time-serially separated into light of respective wavelength regions of R, G and B enters the above mentioned light guide 514 at the entrance end, is led to the tip part 9 through this light guide 514 and is emitted from this tip part 9 to illuminate a part to be observed.

The light from the observed part illuminated by this illuminating light is made to form an image on the solid state imaging device 516 by the objective lens system 515 and is photoelectrically converted. A driving pulse from a driver circuit 531 within the above mentioned video processor is applied to this solid state imaging device 516 through the above mentioned signal line 526 so that reading-out and transfer may be made by this driving pulse. The video signal read out of this solid state imaging device 516 is input into a pre-amplifier 532 provided within the above mentioned video processor or electronic endoscope through the signal line 527. The video signal amplified by this pre-amplifier 532 is input into a processing circuit 533, is processed in this processing circuit 533 to correct γ and remove carriers, to have a knee characteristic against halation parts, to give a bias to dark parts and to be on a pedestal level. The output of the above mentioned processing circuit 533 is converted to a digital signal by an A/D converter 534. This digital video signal is selectively stored in a memory(1) 536a, memory(2) 536b and memory(3) 536c corresponding to respective colors, for example, of red (R), green (G) and blue (B) by a selector 535 through an output range LUT (look-up table) 545 provided with a look-up table for limiting the output range. The outputs of the above mentioned memory(1) 536a, memory(2) 536b and memory(3) 536c are simultaneously read out, are converted to analogue signals by a D/A converter 537 and are output as R, G and B color signals.

A picture frame generating circuit 540 generating a displaying picture frame is provided. The output image signals of the above mentioned D/A converter 537 are combined with the displaying frame by a control signal from this picture frame generating circuit 540 and are output to a superimposing circuit 541 in which patient information input in a character information input circuit 542 is superimposed on the image information. The image signals to which the displaying frame and character information such as the patient information have been thus added are output as R, G and B signals to a matrix circuit 543 and image processing apparatus 560. In the above mentioned matrix circuit 543, the above mentioned R, G and B signals are converted to color difference signals and a luminance signal which are input into an encoder circuit 544 and are converted to an NTSC signal to be output. This NTSC signal is input into the color monitor by which the observed part is color-displayed.

Also, the above mentioned video processor is provided within it with a timing generator 538 making a timing of the entire system and synchronizing the respective circuits of the motor driver 525, driver circuit 531 and memories 536a, 536b and 536c.

The above mentioned image processing apparatus 560 processes the image as shown, for example, in the first to fifth embodiments and outputs the processing result to a displaying device 561 such as a television monitor or video printer in which the image processing result is displayed.

Also, this embodiment is provided with a displaying device discriminating circuit 547 discriminating the kind of the above mentioned displaying device 561 and inputting a displaying device discriminating signal into a data selecting circuit 546 which controls an output range LUT 545 based on the above mentioned displaying device discriminating signal and designates the address of the output range LUT 545 so as to select data different in the respective displaying devices. The above mentioned output range LUT 545 limits the output image signal of the A/D converter 534 to the output range corresponding to the kind of the displaying device 561 based on the designated address data. The output range is limited, for example, by making all the values above the upper limit of the output range upper limit values and making all the values below the lower limit lower limit values.

Even in case the displaying device is only a television monitor or a device different in the displaying capacity is used, a reliable effective data region has not been considered. That is to say, the same image data have been input into any of the displaying devices such as a monitor high in the gradation characteristic and a displaying device narrow in the gradation expression as a monitor or video printer low in the gradation characteristic. Therefore, the displaying capacity has not been able to be well utilized in the displaying device high in the gradation characteristic and the displaying capacity has been so insufficient as to produce an artifact in the displaying device low in the gradation characteristic.

Therefore, in this embodiment, the kind of the displaying device 561 is discriminated by the displaying device discriminating circuit 547 and the effective region of the data is determined by the output range LUT 545 in conformity with the displaying capacity of the displaying device 561.

Thus, according to this embodiment, there are effects that the artifact by the displaying device can be prevented, an accurate process can be made as an image processing system and the diagnosing ability is improved.

The other formations, operations and effects are the same as in the first embodiment.

Figure 16:
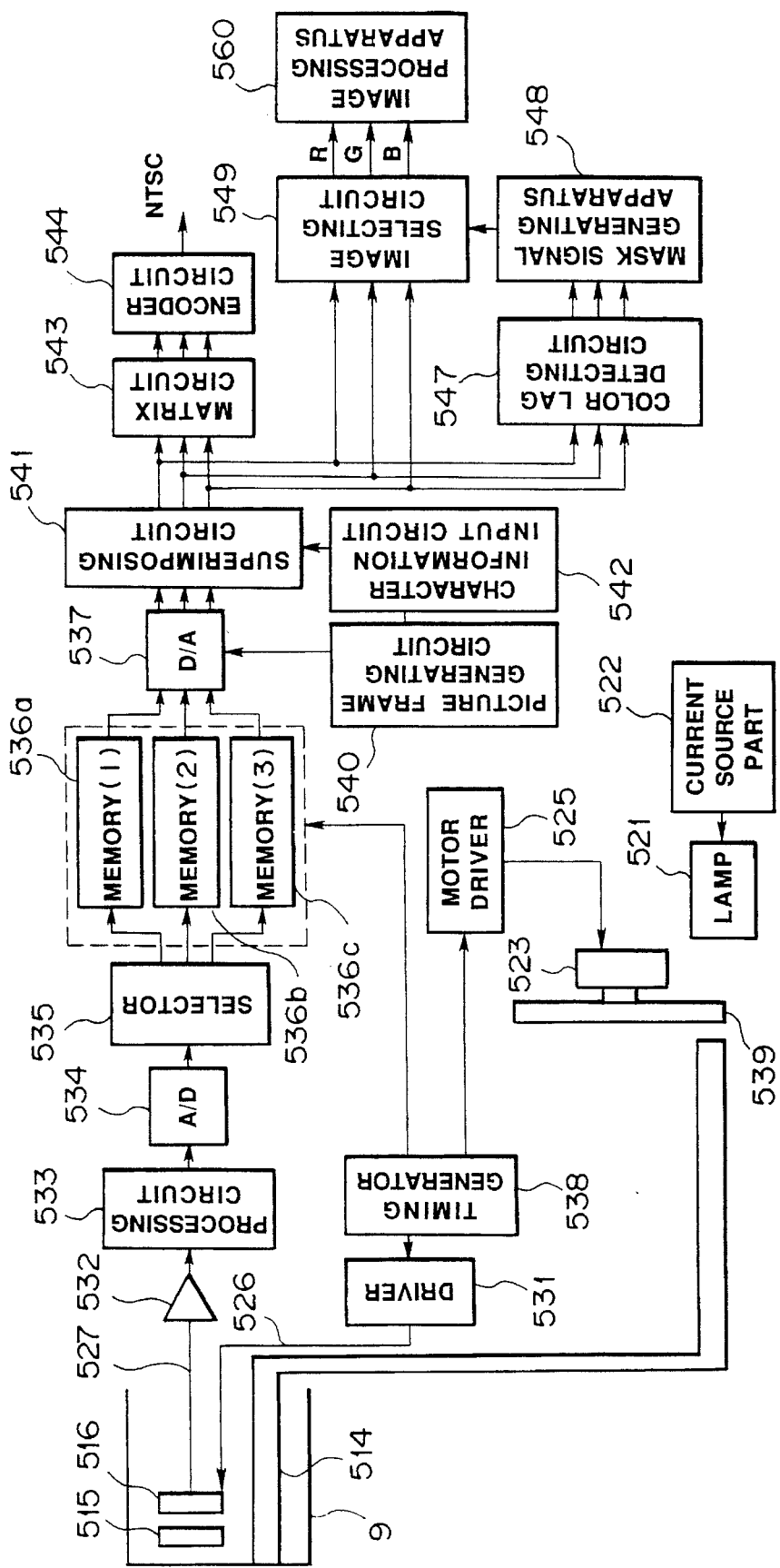
FIGS. 16 to 18 relate to the seventh embodiment of the present invention.
Figure 17:
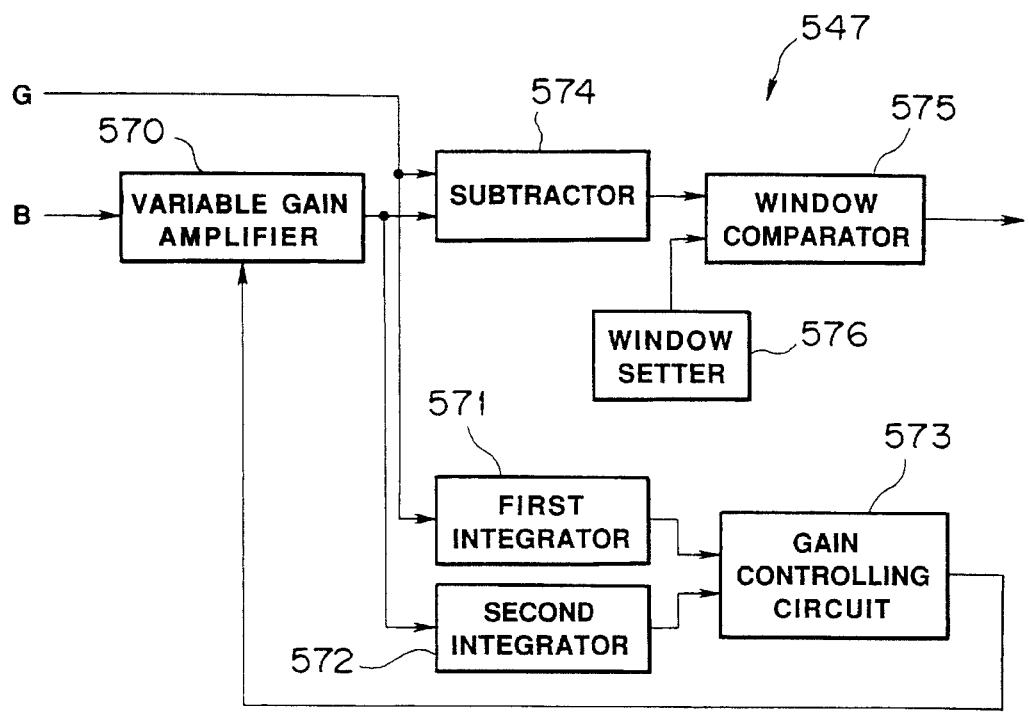
Figure 18:
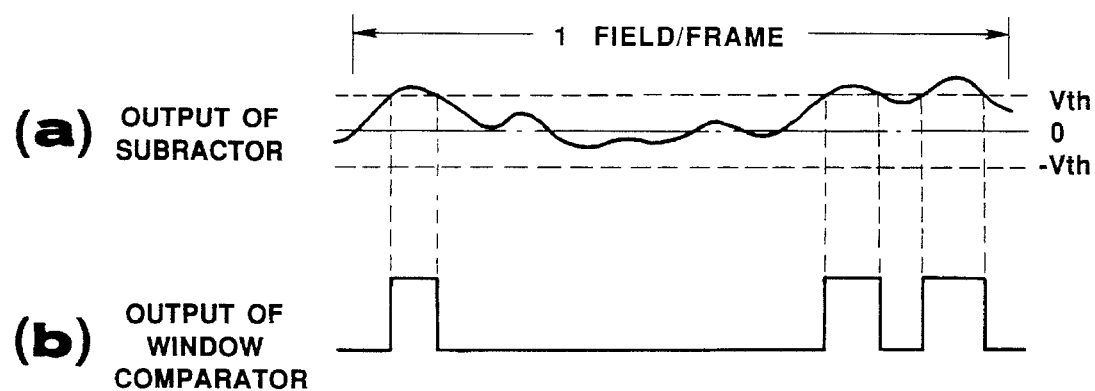

The seventh embodiment of the present invention is shown in FIGS. 16 to 18.

In this embodiment, the output range LUT 545, data selecting circuit 546 and displaying device discriminating circuit 547 in the sixth embodiment are eliminated and the output of the A/D converter 534 is input into the selector 535.

The R, G and B image signals from the superimposing circuit 541 are input into a color lag detecting circuit 547 and image selecting circuit 549. In the frame sequential type endoscope, as the color is time-sequentially separated, in case the movement of the object is fast, a so-called color lag in which the positions of the respective images corresponding to the respective colors will lag to show the primary colors will be generated. The above mentioned color lag detecting circuit 547 detects such color lag amount and the range in which the color lag is produced. This color lag detecting circuit 547 is formed as shown, for example, in FIG. 17. That is to say, the G image signal is input into a first integrator 571 and subtractor 574. The B image signal is input into a second integrator 572 and the above mentioned subtractor 574 through a variable gain amplifier 570. The outputs of both integrators 571 and 572 are input into a gain controlling circuit 573 controlling the gain of the above mentioned variable variable gain amplifier 570. The output of the above mentioned subtractor 574 is input into a window comparator 575. The upper threshold value Vth and lower threshold value −Vth of this window comparator 575 are set by a window setter 576. The output of the above mentioned window comparator 575 is input into a mask signal generating circuit 548 in FIG. 16. In this color lag detecting circuit 547, the G image signal is integrated for 1 field or 1 frame period in the first integrator 571. The B image signal is amplified by the variable gain amplifier 570 and is then integrated for 1 field or 1 frame period in the second integrator 572. The respective outputs of both integrators 571 and 572 are compared with each other in the gain controlling circuit 573. The output of this gain controlling circuit 573 controls the gain of the variable gain amplifier 570 so that the respective outputs of both integrators 571 and 572 may be equal to each other. As a result, the G image signal and B image signal input into the subtractor 574 will become equal in the integrated value within 1 field or 1 frame period. The G image signal and B image signal are so high in correlation that, as shown in FIG. 18(a), the output of the above mentioned subtractor 574 will approach 0 in case no color lag is produced but the absolute value will become large in case a color lag is produced. As shown in FIG. 18(b), the window comparator 575 will output an H level signal in case the output of the above mentioned subtractor 574 deviates from the range from Vth to −Vth but will output an L level signal in the other case. Therefore, the region in which the output of the above mentioned window comparator 575 is on the H level is the region in which the color lag is large.

The above mentioned color lag detecting circuit 547 controls the mask signal generating circuit 548 so that, in case the color lag amount is above a set value, a mask signal as ineffective region data may be generated from the mask signal generating circuit 548. This mask signal is input into the above mentioned image selector circuit 549. This image selecting circuit 549 selects the original image from the superimposing circuit 541 on the region in which there is no or little color lag but selects the mask signal generated from the mask signal generating circuit 548 on the region in which the color lag detected by the color lag detecting circuit 547 is produced and transmits them to the image processing apparatus 560.

When the images of the respective wavelength bands obtained by the frame sequential type endoscope are operated, the part in which a color lag is produced will produce an artifact.

Therefore, in this embodiment, the region in which a color lag is produced is detected by the color lag detecting circuit 547 and the image signal of this region is substituted with a mask signal so that the effective region and ineffective region as a result of processing the image may be definitely distinguished from each other.

The other formations, operations and effects are the same as in the sixth embodiment.

Figure 19:
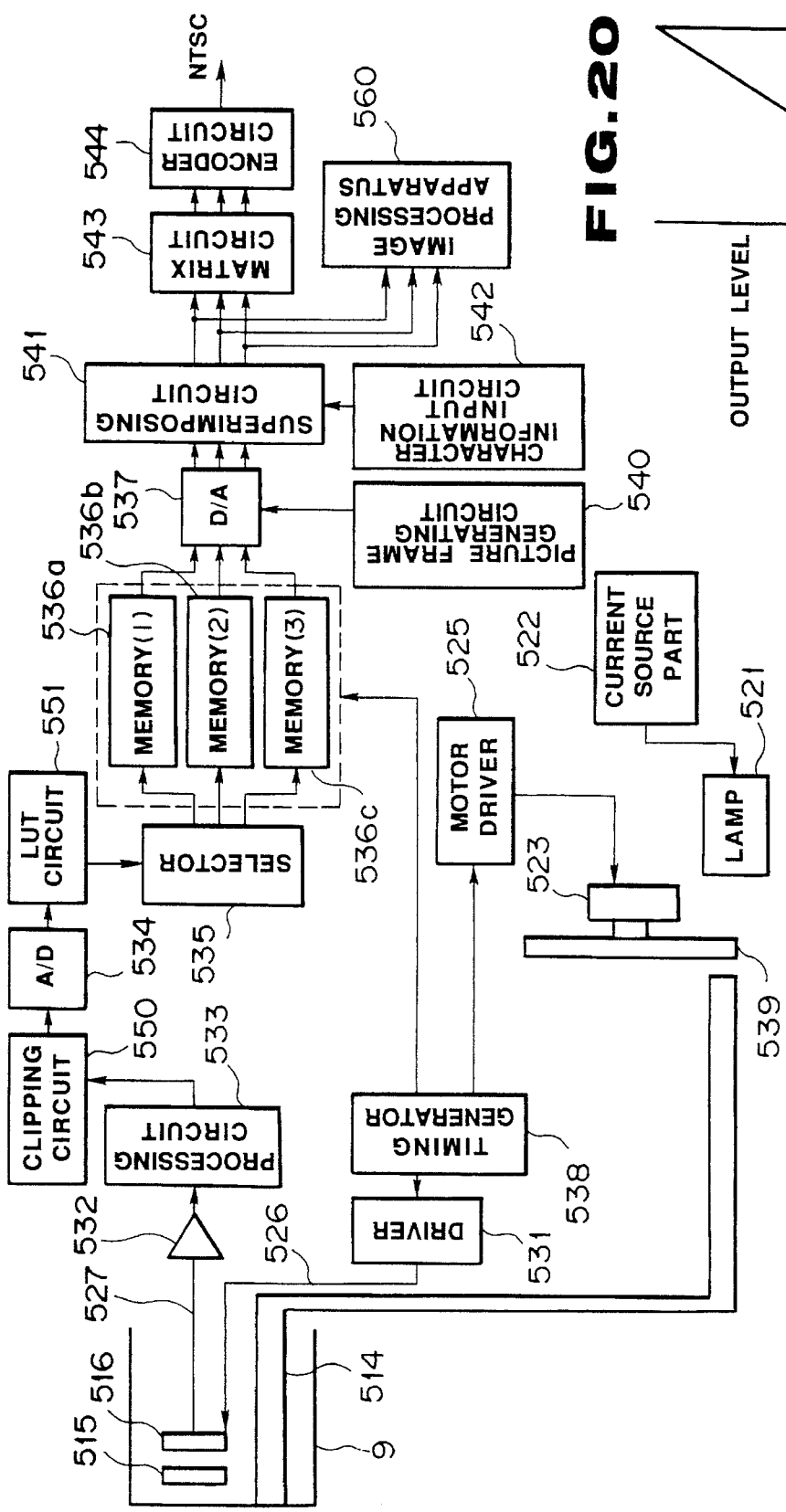
FIGS. 19 and 20 relate to the eighth embodiment of the present invention.
Figure 20:
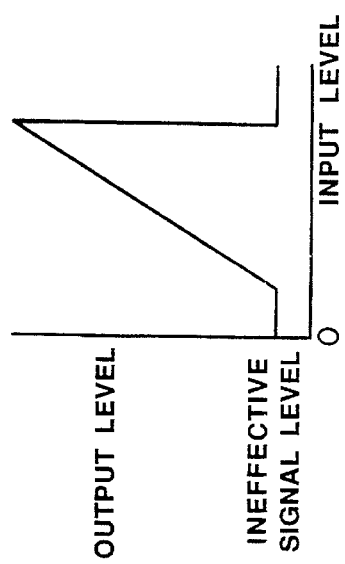

In FIGS. 19 and 20 is shown the eighth embodiment of the present invention.

In this embodiment, the output range LUT 545, data selecting circuit 546 and displaying device discriminating circuit 547 in the sixth embodiment are eliminated and the output of the processing circuit 533 is input into the selector 535 through a clipping circuit 550, A/D converter 534 and LUT circuit 551.

The image signal output from the processing circuit 533 is input into the clipping circuit 550 in which the low level image signal low in S/N and lacking in the reliability and the high level image signal such as of the over-exposure and halation part are clipped respectively to fixed values. Thus, the ineffective data are made a fixed value by the clipping circuit 550, are converted to digital data by the A/D converter 534 and are input into the LUT circuit 551. In this LUT circuit 551, the data are converted by input and output characteristics as are shown in FIG. 20. That is to say, the low level part and high level part clipped to the fixed values in the clipping circuit 550 are both converted to fixed ineffective signal levels. The thus converted image signals are input into the selector 535. The high level data among the image data are in non-linear input and output relations in the processing circuit 533 having a knee characteristic due to a halation part or very high exposure level. In the dark part, due to the lack of exposure, the image signal will be on a low level, therefore the S/N will reduce and the image data will be low in reliability. If an image is processed or measured by using such a high level or low level data, an artifact will likely to be produced.

Therefore, in this embodiment, the low level part and high level part are clipped to fixed values in the clipping circuit 550 and are converted to a fixed ineffective signal level in the LUT circuit 551 so that, in the image as a result of processing the image, as the ineffective region will be displayed as a uniform region peculiar to the ineffective region, the effective region and ineffective region may be definitely discriminated and the diagnosing ability may improve.

The effective data range set in the clipping circuit 550 may be altered to be a precision range required for the respective using objects in response to such respective using objects as the observation, image processing and measurement.

The other formations, operations and effects are the same as in the sixth embodiment.

Figure 21:
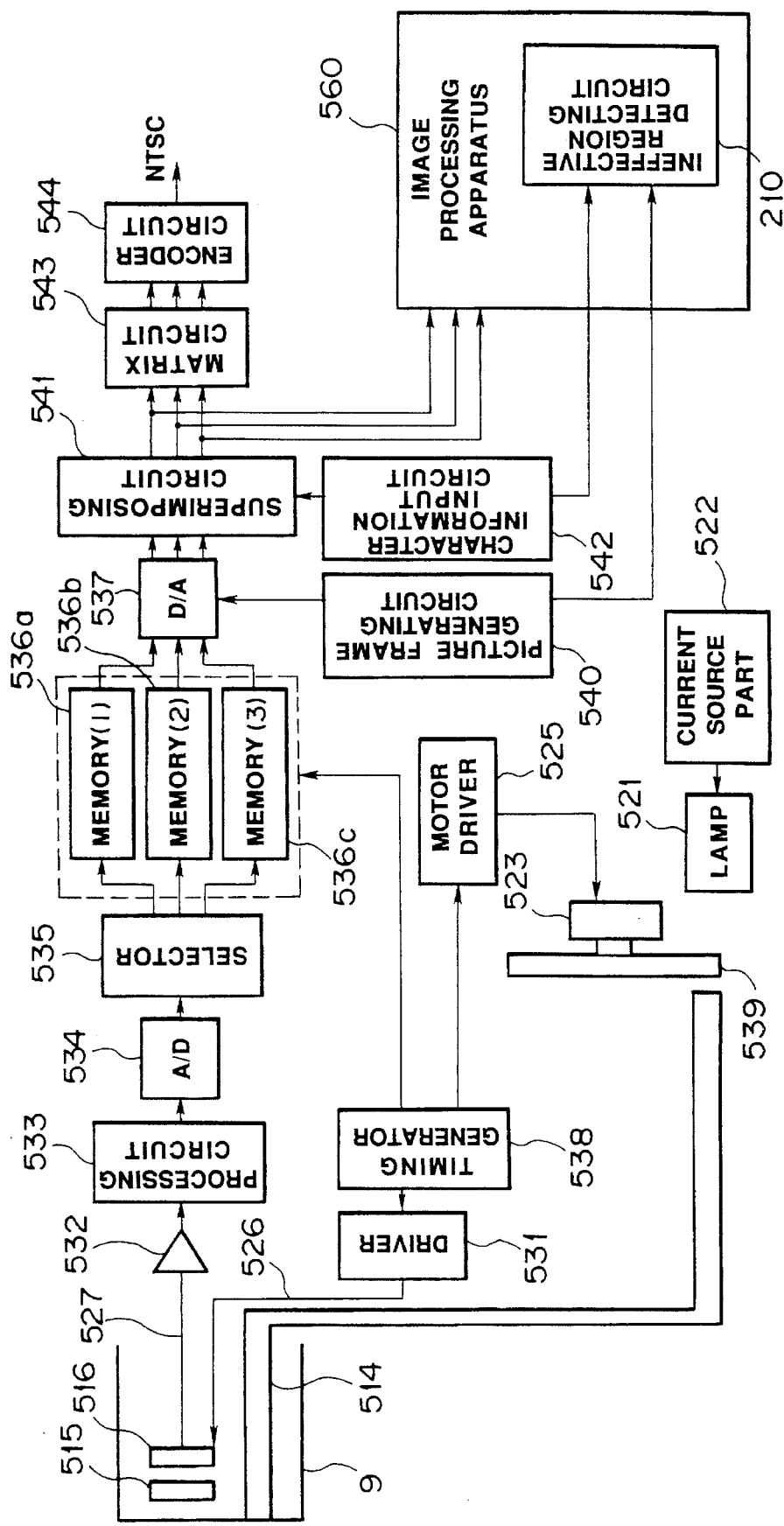
FIG. 21 is a block diagram showing the formation of an endoscope apparatus in the ninth embodiment of the present invention.

FIG. 21 shows the ninth embodiment of the present invention.

In this embodiment, the output range LUT 545, data selecting circuit 546 and displaying device discriminating circuit 547 in the sixth embodiment are eliminated and the output of the A/D converter 534 is input into the selector 535.

The image processing apparatus 560 is of substantially the same formation as of the image processing part 108 shown in FIG. 1 but, instead of the outputs of the logarithmic amplifier, differential amplifier and subtracter, the respective outputs of a picture frame generating circuit 540 and character information input circuit 542 are input into the ineffective region detecting circuit 210 in this embodiment.

All the signals among the image signals output from the endoscope apparatus are not always effective. That is to say, such character information as of the picture frame and patient data is not required to have the image processed and, unless such information is definitely separated from the image data imaged by the endoscope, the data after the image is processed will be meaningless. If such character information as of the picture frame and patient data and the effective region are discriminated from each other by software on the image processing apparatus side, the processing speed will be reduced.

Therefore, in this embodiment, the output of the picture frame generating circuit 540 generating the picture frame information and the output of the character information inputting circuit 542 inputting such character information as the patient data are input into the ineffective region detecting circuit 210 within the image processing apparatus 560 and the effective region required for the image process and the ineffective region not required for the image process are discriminated from each other by this ineffective region detecting circuit 210. Thereby, the effective region and ineffective region can be discriminated and output, the diagnosing ability can be improved by eliminating the artifact, the burden on the software of the image processing apparatus 560 can be alleviated and a high speed process is possible.

The effective region and ineffective region may be altered in response to such using objects as the observation, image process and measurement.

The other formations, operations and effects are the same as in the first or sixth embodiment.

Figure 22:
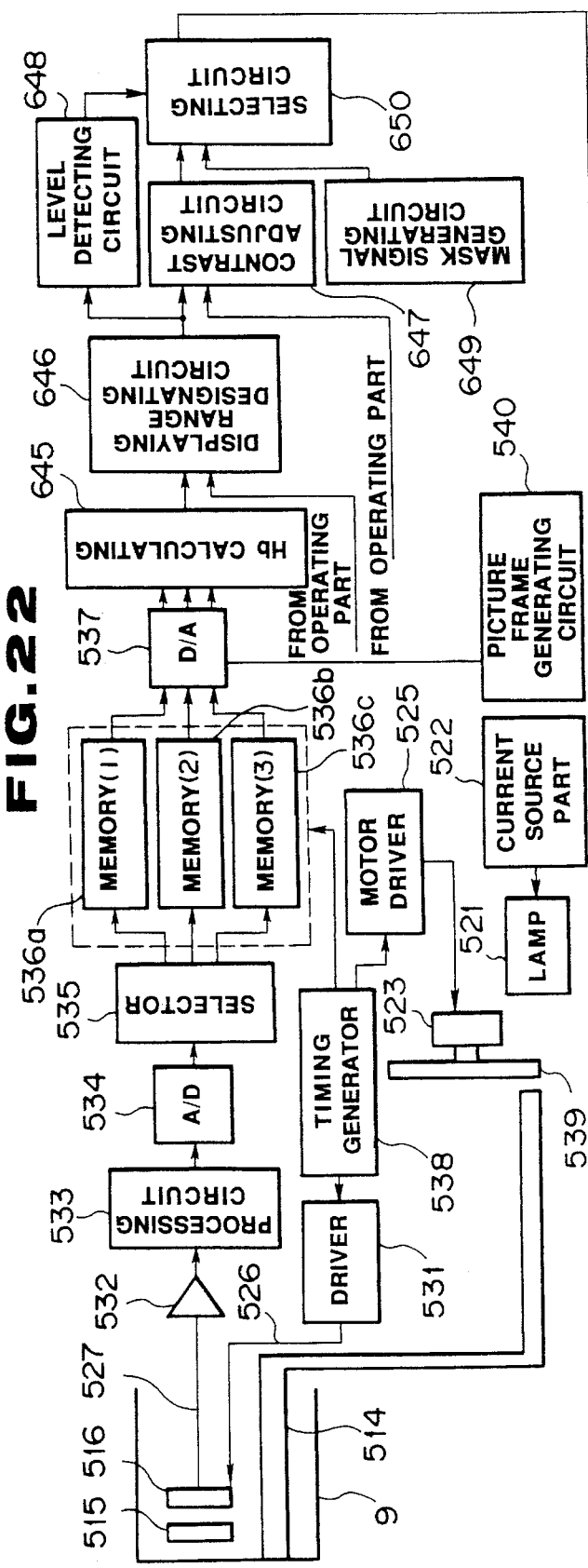
FIGS. 22 and 23 relate to the tenth embodiment of the present invention.
Figure 23:
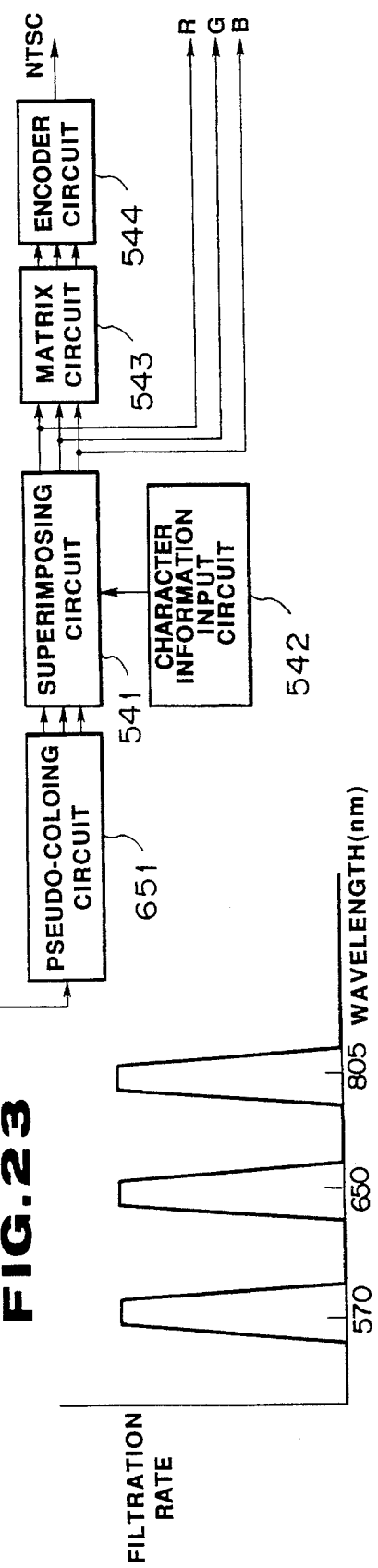

In FIGS. 22 and 23 is shown the tenth embodiment of the present invention.

In this embodiment, the ineffective region and effective region are discriminated after the image is processed.

In this embodiment, as shown in FIG. 23, the respective filters of the rotary filter 539 transmit light of narrow bands having 570 mn, 650 nm and 805 nm respectively as centers.

Also, in this embodiment, the output range LUT 545, data selecting circuit 546 and displaying device discriminating circuit 547 in the sixth embodiment are eliminated and the output of the A/D converter 534 is input into the selector 535. Also, the formations after the D/A converter 537 are different from those of the sixth embodiment. That is to say, the image data of the respective wavelength regions output from the D/A converter 537 are input into an Hb calculating circuit 645. This Hb calculating circuit 645 is to calculate the distribution of the hemoglobin (which shall be mentioned as Hb) of a living body. In this Hb calculating circuit 645, the same as in the operation in the third embodiment, the logarithms of the respective image data video-imaged by the respective illuminating light transmitted through the filter having 570 nm as a center transmitted wavelength and the filter having 805 nm as a center transmitted wavelength are calculated and then the level difference is calculated. The Hb distribution calculated by the above mentioned Hb calculating circuit 645 is input into a displaying range designating circuit 646 which designates the range of the Hb concentration to be displayed. This range can be varied by an operating part (not illustrated) provided in the video processor 6.

The Hb distribution image having had the displaying range designated by the above mentioned displaying range designating circuit 646 is input into a contrast adjusting circuit 647 and level detecting circuit 648. The above mentioned contrast adjusting circuit 647 is to adjust the Hb distribution in the range designated by the displaying range designating circuit 646 so as to be of the contrast optimum to the observation. The contrast can be adjusted by the operating part (not illustrated) provided in the video processor. The Hb distribution image adjusted in the contrast by the above mentioned contrast adjusting circuit 647 is input into a selecting circuit 650. On the other hand, the above mentioned level detecting circuit 648 detects the level of the image data output from the displaying range designating circuit 646 and controls the above mentioned selecting circuit 650. That is to say, the level detecting circuit 648 detects the image level producing an artifact in case the image is displayed in the monitor and controls the selecting circuit 650 so that, with respect to the image signal part having the detected image level, the selecting circuit 650 may input not the signal from the contrast adjusting circuit 647 but the signal of the mask signal generating circuit 649.

In the above mentioned selecting circuit 650, the ineffective region producing an artifact is replaced with a mask signal and thus the image signal in which the effective Hb distribution image region and the ineffective region producing an artifact are definitely discriminated is processed to be pseudo-colorized in response to the level of the image signal in a pseudo-colorizing circuit 651. The Hb distribution image from this pseudo-colorizing circuit 651 is input into the superimposing circuit 541 and the patient information input in the character information input circuit 542 is superimposed on the image information. The image signal to which such character information as of the displaying frame and patient information is thus added is output as R, G and B signals which are input into a matrix circuit 543. In this matrix circuit 543, the above mentioned R, G and B signals are converted to color difference signals and a luminance signal which are input into an encoder circuit 544 and are converted to an NTSC signal to be output. The above mentioned NTSC signal is or the R, G and B signals are input into the color monitor in which the Hb distribution image is displayed in the pseudo-color.

Thus, in this embodiment, after the Hb distribution is processed to be calculated, the region of the image level producing an artifact is detected and is displayed by other than the normal displaying method and therefore misconception can be prevented as to the result of processing the image.

The other formations, operations and effects are the same as in the sixth embodiment.

Figure 24:
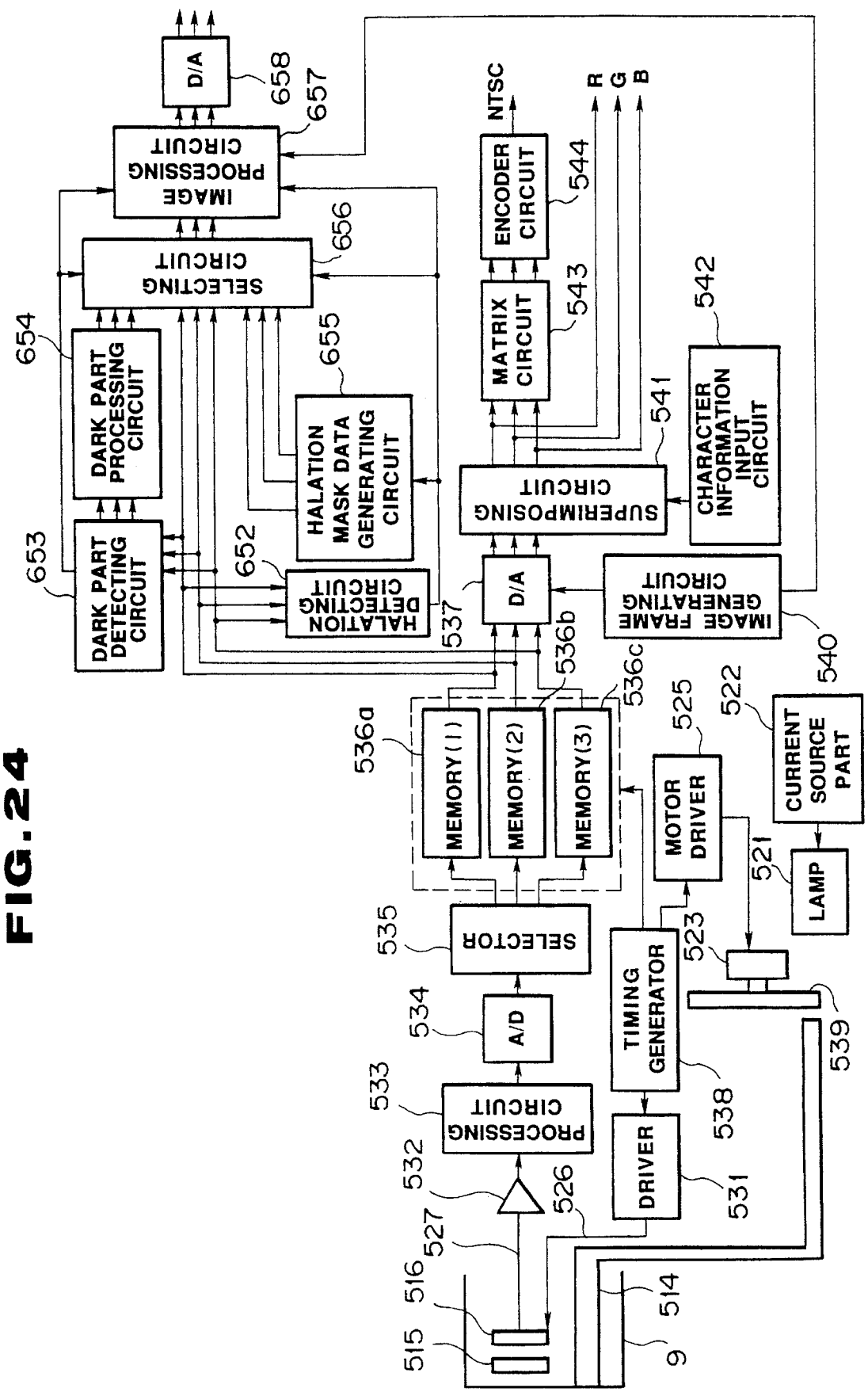
FIG. 24 is a block diagram showing the formation of an endoscope apparatus in the 11th embodiment of the present invention.

In FIG. 24 is shown the 11th embodiment of the present invention.

This embodiment is different from the tenth embodiment in the formations in and after the memories 536a, 536b and 536c.

In this embodiment, the image signals output from the respective memories 536a to 536c are input into the D/A converter 537, selecting circuit 656, halation detecting circuit 652 and dark part detecting circuit 653.

The displaying frame by the image frame generating circuit 540 is combined with the output image signal of the above mentioned D/A converter 537. In the superimposing circuit 541, the patient information input into the character information input circuit 542 is superimposed on the image information. The image signal, to which the character information such as the displaying frame and patient information is thus added, is output as R, G and B signals which are output as an NTSC signal through the matrix circuit 543 and encoder circuit 544.

The output of the above mentioned selecting circuit 656 is processed to be an image for calculating the same Hb distribution as in the tenth embodiment in the image processing circuit 657. The output of this image processing circuit 657 is converted to an analogue signal by the D/A converter 658 and is output.

The above mentioned dark part detecting circuit 653 detects the part in which the levels of the respective images output from the above mentioned memories 536a to 536c are low, the illumination is not sufficient and the S/N is low. This dark part detecting circuit 653 transmits image data to the dark part processing circuit 654 and controls the selecting circuit 656 and image processing circuit 657. In the above mentioned dark part processing circuit 654, with respect to the dark part detected in the above mentioned dark part detecting circuit, the original image is worked and is transmitted to the selecting circuit 656. For the original image working process, for example, a noise removing process is made with a low-pass filter and then a process for equalizing the image levels of the respective parts is made. The above mentioned dark part detecting circuit 653 controls the selecting circuit 656 so that, with respect to the detected dark part, instead of the image data from the memories 536a to 536c, the image data from the dark part processing circuit 654 may be selected. With respect to the observed part detected by the dark part detecting circuit 653 and not sufficiently illuminated, no sufficient reliability as of the Hb distribution image will be obtained. Therefore, such parts are made equal in the image levels by the dark part processing circuit 654 so that it may be recognized that they have no Hb present and are dark parts.

On the other hand, the halation detecting circuit 652 detects as a halation part the part extremely different from the periphery and saturated with image data levels among the image data output from the memories 536a to 536c. This halation detecting circuit 652 controls the selecting circuit 656 and image processing circuit 657. That is to say, when the halation detecting circuit 652 detects a halation part, it will output to the selecting circuit 656 the halation mask data stored in the ROM of the halation mask data generating circuit 655 and will control the selecting circuit 656 to select the mask data from the halation mask data generating circuit 655 instead of the image data from the memories 536a to 536c.

With respect to neither dark part nor halation part which is but to the image data part reliable, the above mentioned selecting circuit 656 selects the image data from the memories 536a to 536c as they are stored. With respect to the dark part detected by the dark part detecting circuit 653 and the halation part detected by the halation detecting circuit 652, the selecting circuit 656 selects the image signal processed by the dark part processing circuit 654 and the image signal of the mask data output from the halation mask data generating circuit 655.

The image data selected by the selecting circuit 657 are processed by the image processing circuit 657 to make an Hb distribution image. The respective output signals from the dark part detecting circuit 653, halation detecting circuit 652 and image frame generating circuit 540 are input as control signals into the selecting circuit 656. The image processing circuit does not process on the basis of the signals from the respective detecting circuits 653 and 652 the already detected dark part and halation part but outputs the signal from the dark part processing circuit 654 and the signal from the halation mask data generating circuit 655 as they are to the D/A comparator 658. Also, the image processing circuit 657 does not process the data outside the picture frame not required to be processed as an Hb distribution image.

The Hb distribution image data processed and obtained by the above mentioned image processing circuit 657 are converted to an analogue image signal by the D/A converter 658 and are output to a monitor or the like.

Thus, in this embodiment, only the region reliable as the Hb distribution data is processed to calculate the Hb distribution but such other ineffective regions as the dark parts, data outside the picture frame and halation parts are processed differently so that the effective region and ineffective region may be discriminated from each other, the Hb distribution may be prevented from being misconceived and the observing ability may be improved to make an accurate diagnosis possible.

When the image on which the character information has been superimposed by the superimposing circuit 541 in FIG. 24 is to be processed by the image processing circuit 657, the signal from the character information input circuit 542 may be transmitted to the image processing circuit 657 and the character information part may be processed to be an image by this image processing circuit 657.

The other formations, operations and effects are the same as in the tenth embodiment.

Figure 25:
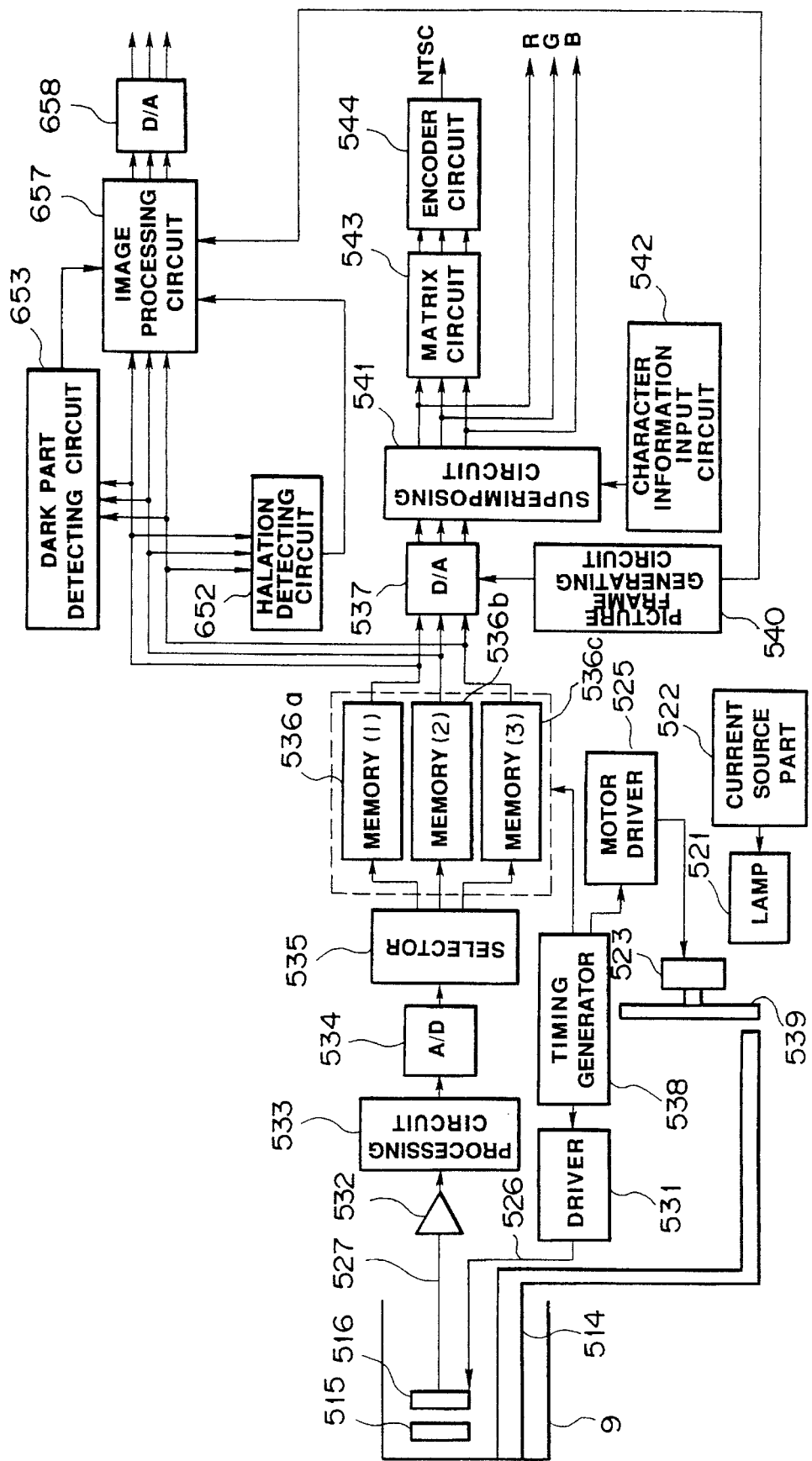
FIG. 25 is a block diagram showing the formation of an endoscope apparatus in the 12th embodiment of the present invention.
Figure 26:
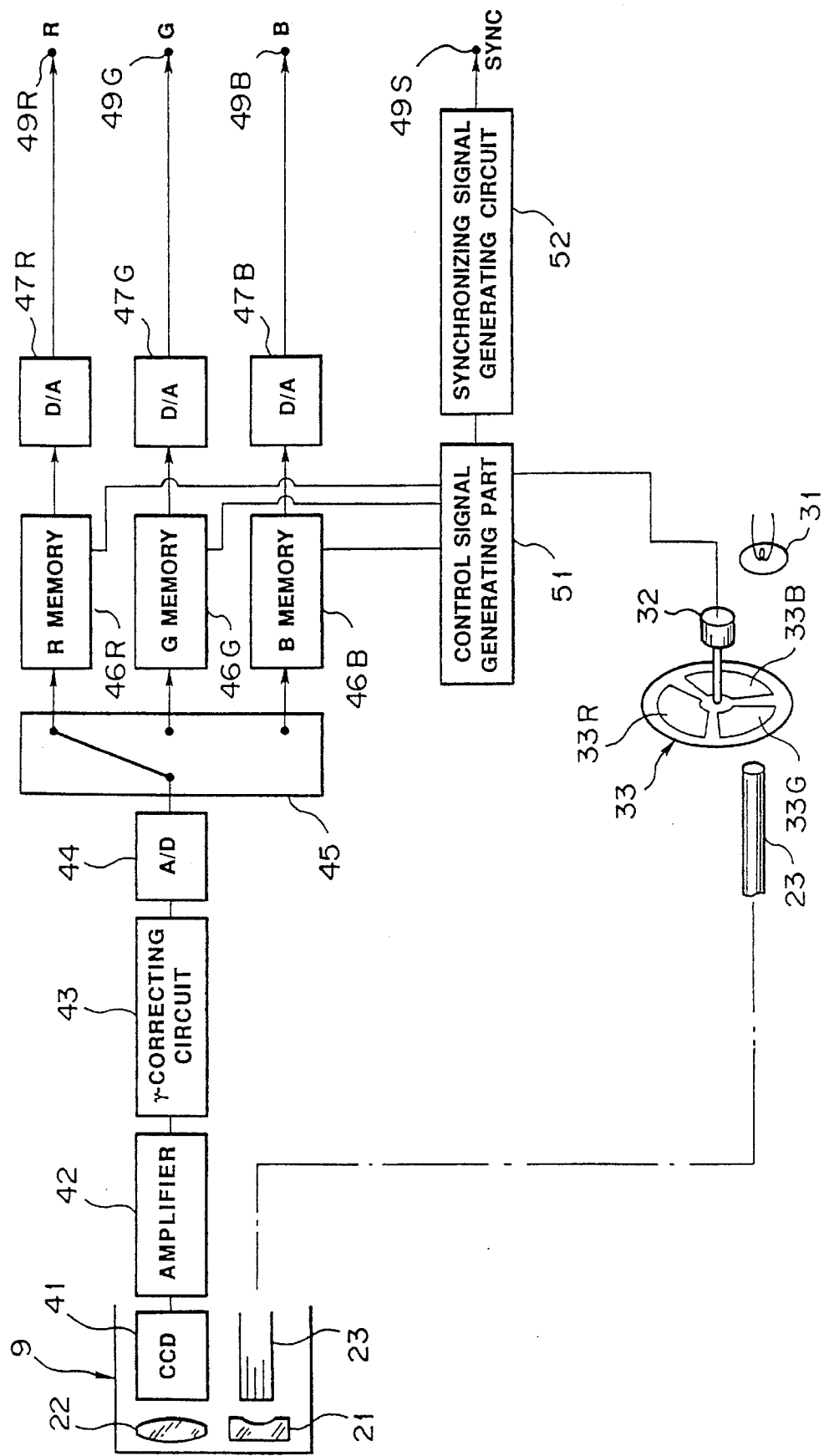
FIG. 26 is a block diagram showing the formation of a conventional endoscope apparatus.

FIG. 25 shows the 12th embodiment of the present invention.

In this embodiment, the dark part processing circuit 654, halation mask data generating circuit 655 and selecting circuit 656 in the 11th embodiment are eliminated and the image data output from the memories 536a to 536c are input as they are into the image processing circuit 657. Also, the respective outputs of the dark part detecting circuit 653 and halation detecting circuit 652 are input into this image processing circuit 657.

The above mentioned image processing circuit 657 processes the Hb distribution to be pseudo-colorized. The processing method is the same as in the third embodiment. In this image processing circuit 657, on the basis of the respective outputs of the above mentioned dark part detecting circuit 653 and halation detecting circuit 652, with respect to the ineffective regions of the dark parts and halation parts, the above described Hb distribution is not processed to be pseudo-colorized but is output as it is so that, if colors not appearing in the original image are used as colors to be used in the pseudo-colorizing process, the effective region and ineffective region may be discriminated from each other.

In the above mentioned image processing circuit 657, with respect to the ineffective regions of the dark parts and halation parts, the Hb distribution may not be processed to be pseudo-colorized but the original image may be output as a monochromatic image. The original image can be made a monochromatic image by producing a luminance signal from the input R, G and B signals and equalizing the levels of the R, G and B signals on the basis of this luminance signal.

Thus, according to this embodiment, with respect to the effective region high in the reliability, the Hb distribution will be displayed in the pseudo-colors but, with respect to the dark part and halation part low in reliability, the original image will be displayed as it is as a monochromatic image and therefore, in the processed image, the effective region and ineffective region can be discriminated from each other and, on the ineffective region, the cause of being ineffective can be directly recognized.

The other formations, operations and effects are the same as in the 11th embodiment.

The present invention is not limited to the above mentioned respective embodiments and does not have the processes limited to those shown in the respective embodiments but can be applied to the structure enhancing process as by flattening the histogram and to the measurement and the like.

The endoscope to which the present invention can be applied may be of a type having a solid state imaging device at the tip or of a type in which the image is led out of the observed object through an image guide by optical fibers and is imaged by an imaging device.

Also, the present invention can be applied not only to the endoscope but also, for example, to the case that an externally fitted television camera is fitted to a microscope and the video signal is processed to be an image and the case that such draft as a film is converted to a video signal by using a scanner and this video signal is processed to be an image.

As explained above, according to the present invention, the image can be processed or the ineffective image and effective image relating to the result of processing the image can be discriminated and therefore there are effects that the region not meeting the required precision can be discriminated, misconception can be prevented from being generated and information high in reliability can be obtained.

It is apparent that, in this invention, working modes different in a wide range can be formed on the basis of this invention without deviating from the spirit and scope of the invention. This invention is not restricted by its specific working mode except being limited by the appended claims.

What is claimed is:

1. An electronic endoscope apparatus comprising:

a light source for illuminating an interior portion of a biological body under medical examination;

filter means selectively interposed between the light source and illuminated interior portion of the biological body for filtering out light having a preselected transmission wavelength, and for projecting said filtered light to the interior portion thereof;

image sensor means for imaging the illuminated interior portion by receiving the filtered light therefrom to thereby produce a functional information image signal;

means for processing said functional information image signal so as to detect a region having an exposure level exceeding over an allowable maximum exposure level, and for superimposing said region having the over-exposure level on said functional information image signal; and means for displaying both a functional information image of the biological body and said over-exposure region superimposed thereon based upon said functional information image signal and said over-exposure region.

2. An electronic endoscope apparatus as claimed in claim 1, wherein said processing/superimposing means includes:

a calculation unit for calculating functional information data from said functional information image signal;

a detection unit for detecting said over-exposure region from said functional information image data; and a superimposing unit for superimposing said over-exposure region on said functional image.

3. An electronic endoscope apparatus as claimed in claim 2, wherein said detecting unit includes a comparator for value so as to detect whether or not said exposure level of the area exceeds over said allowable maximum exposure level, whereby said over-exposure region is detected.

4. An electronic endoscope apparatus as claimed in claim 2, wherein said superimposing unit includes:

an address memory for storing said over-exposure region; and a superimposing circuit for superimposing said overexposure region on said functional information image signal based upon said stored address.

5. An electronic endoscope apparatus as claimed in claim 1, wherein said filter means includes a disk and at least a first interference filter having a first transmission wavelength and a second interference filter having a second transmission wavelength.

6. An electronic endoscope apparatus as claimed in claim 1, wherein said functional image represents one of hemoglobin concentration and oxygen saturation of hemoglobin.

* * * * *